(12) United States Patent
Chan et al.

(10) Patent No.: US 11,248,255 B2
(45) Date of Patent: Feb. 15, 2022

(54) AMPLIFICATION OF NANOPARTICLE BASED ASSAY

(71) Applicant: The Governing Council of the University of Toronto, Toronto (CA)

(72) Inventors: Warren C. W. Chan, Toronto (CA); Jisung Kim, Richmond Hill (CA); Kyrylo Zagorovsky, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 479 days.

(21) Appl. No.: 15/185,788

(22) Filed: Jun. 17, 2016

(65) Prior Publication Data

US 2017/0022547 A1 Jan. 26, 2017

Related U.S. Application Data

(60) Provisional application No. 62/181,907, filed on Jun. 19, 2015.

(51) Int. Cl.
| | |
|---|---|
| *C12Q 1/68* | (2018.01) |
| *C12Q 1/6825* | (2018.01) |
| *C12Q 1/6848* | (2018.01) |
| *C12Q 1/6818* | (2018.01) |
| *C12Q 1/6834* | (2018.01) |

(52) U.S. Cl.
CPC ......... *C12Q 1/6825* (2013.01); *C12Q 1/6818* (2013.01); *C12Q 1/6834* (2013.01); *C12Q 1/6848* (2013.01)

(58) Field of Classification Search
CPC ........ C12Q 2531/101; C12Q 2537/143; C12Q 2563/137; C12Q 2563/155; C12Q 1/6816; C12Q 1/6825; C12Q 1/6818; C12Q 1/6834; C12Q 1/6848; C12Q 1/6844
See application file for complete search history.

(56) References Cited

U.S. PATENT DOCUMENTS

| | | | |
|---|---|---|---|
| 6,544,732 B1 * | 4/2003 | Chee | B82Y 15/00 435/174 |
| 10,345,240 B2 * | 7/2019 | Chan | G01N 21/6458 |
| 2002/0042125 A1 * | 4/2002 | Petersen | B01L 3/502715 435/287.2 |
| 2005/0130188 A1 * | 6/2005 | Walt | B01J 19/0046 506/3 |
| 2009/0061450 A1 * | 3/2009 | Hunter | B01L 3/502715 435/6.11 |

(Continued)

OTHER PUBLICATIONS

Giri, S. et al. (2011) Rapid screening of genetic biomarkers of infectious agents using quantum dot barcodes. ACS Nano 5:1580-1587.

(Continued)

*Primary Examiner* — Betty J Forman
(74) *Attorney, Agent, or Firm* — Stoel Rives LLP; Jordan B. Olsen

(57) ABSTRACT

An automated multiplex detector system includes: (a) a nucleic acid amplification compartment for amplifying nucleic acid of one or more targets in a sample, and (b) an analysis compartment in fluid communication with the amplification compartment, the analysis compartment housing a nanoparticle-based multiplex detector capable of using the amplified nucleic acid of the amplification compartment and producing a signal that correlates with the presence of the one or more targets in the sample.

13 Claims, 24 Drawing Sheets

Specification includes a Sequence Listing.

(56) References Cited

U.S. PATENT DOCUMENTS

| | | | | |
|---|---|---|---|---|
| 2009/0253181 | A1* | 10/2009 | Vangbo | G01N 27/44791 435/91.1 |
| 2009/0325276 | A1* | 12/2009 | Battrell | B01L 3/502715 435/287.2 |
| 2010/0035349 | A1* | 2/2010 | Bau | B01L 3/50273 436/43 |
| 2010/0291666 | A1* | 11/2010 | Collier | B01L 3/502715 435/287.2 |
| 2011/0137018 | A1* | 6/2011 | Chang-Yen | G01N 35/0098 530/412 |
| 2011/0207137 | A1* | 8/2011 | Malik | G01N 21/6428 435/6.12 |
| 2013/0331298 | A1* | 12/2013 | Rea | C12Q 1/6844 506/16 |

OTHER PUBLICATIONS

Kolostranec, J.M. et al. (2007) Convergence of quantum dot barcodes with microfluidics and signal processing for multiplexed high-throughput infectious disease diagnostics. Nano Letters 7:2812-2818.

Han, M. et al. (2001) Quantum-dot-tagged microbeads for multiplexed optical coding of biomolecules. Nature Biotechnology, 19:631-635.

Fournier-Bidoz, S. et al. (2008) Facile and rapid one-step mass preparation of quantum-dot barcodes. Angewandte Chemie International Edition English 47:5577-5581.

Walt, D.R. (2010) Fibre optic microarrays. Chemical Society Review, 39:38-50.

Piepenburg, O. et al. (2006) DNA detection using recombination proteins. PLoS Biology, 4:e204.

Liong, M. et al. (2013) Magnetic barcode assay for genetic detection of pathogens. Nature Communications, 4:1752.

Zhu, H. et al. (2011) Optofluidic fluorescent imaging cytometry on a cell phone. Analytical Chemistry, 83:6641-6647.

Peng, X. et al. (1997) Epitaxial growth of highly luminescent CdSe / CdS core / shell nanocrystals with photostability and electronic accessibility. Journal of the American Chemical Society, 119:7019-7029.

Hines, M.A., Guyot-Sionnest, P. (1996) Synthesis and characterization of strongly luminescing ZnScapped CdSe nanocrystals. Journal of Physical Chemistry, 100:468-471.

Smith G.J.D. et al. (2009) Dating the emergence of pandemic influenza viruses. Proceedings of the National Academy of Sciences of the United States of America, 106:11709-11712.

Yerly, S. et al. (2001) Nosocomial outbreak of multiple bloodborne viral infections. The Journal of Infectious Diseases, 184:369-372.

Chu, C. et al. (2001) Hepatitis C: Comparison with acute hepatitis B—Comparison of clinical, 355 virologic and pathologic features in patients with acute hepatitis B and C. Journal of Gastroenterology and Hepatology 16:209-214.

McDonald, J.C. et al. (2000) Fabrication of microfluidic systems in poly(dimethylsiloxane). Electrophoresis, 21:27-40.

Duffy, D.C. et al. (1998) Rapid prototyping of microfluidic systems in poly(dimethylsiloxane). Analytical Chemistry, 70:4974-4984.

* cited by examiner

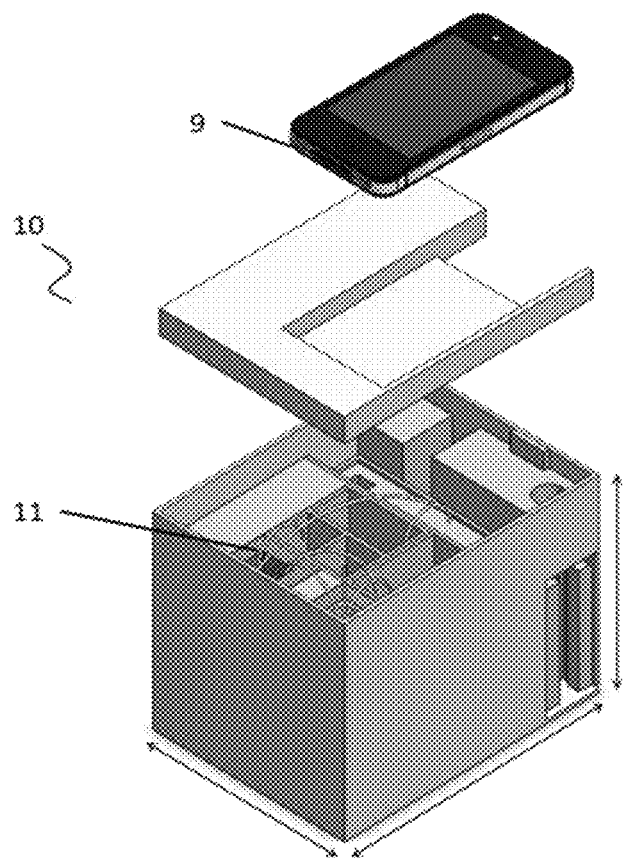
Fig. 1A
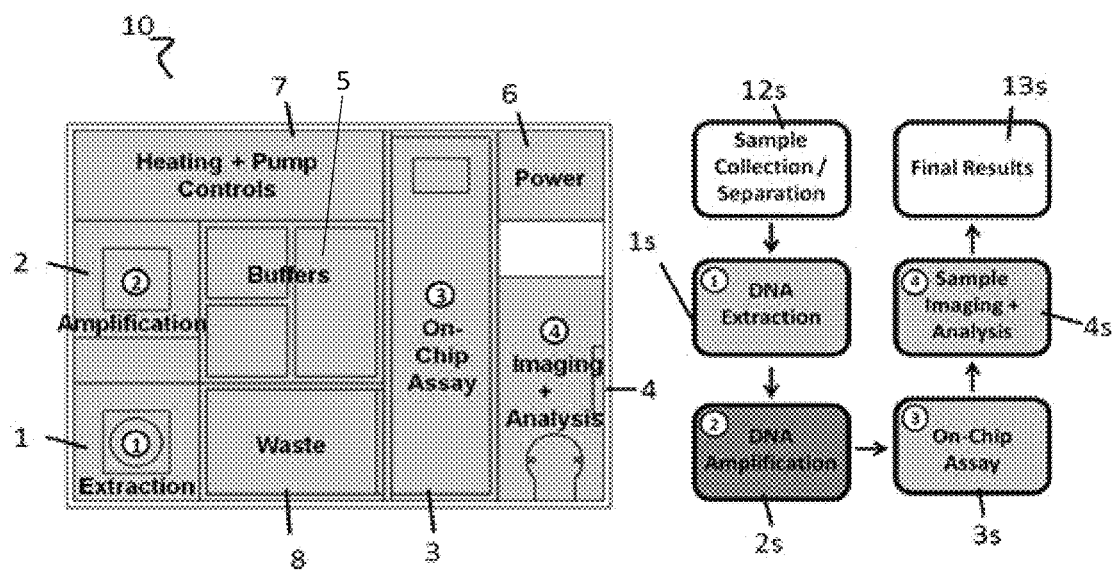
Fig. 1B
Fig. 1C

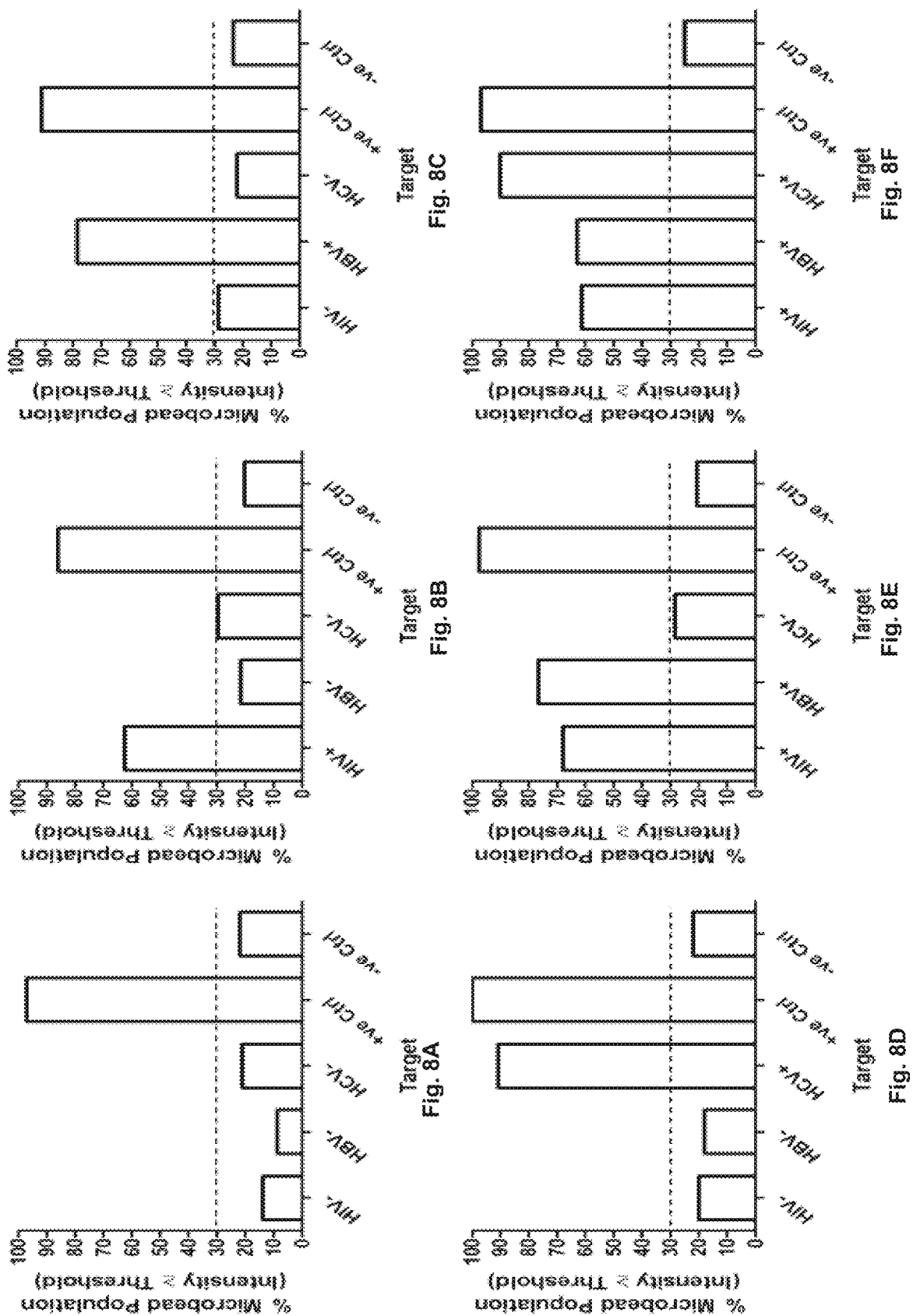

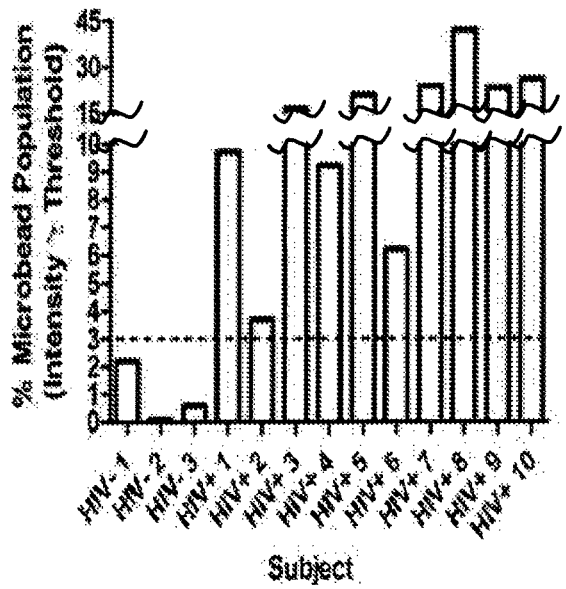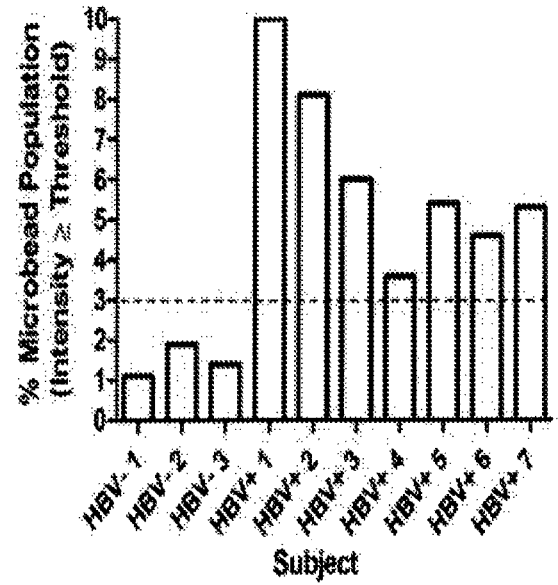
Fig. 9A    Fig. 9B
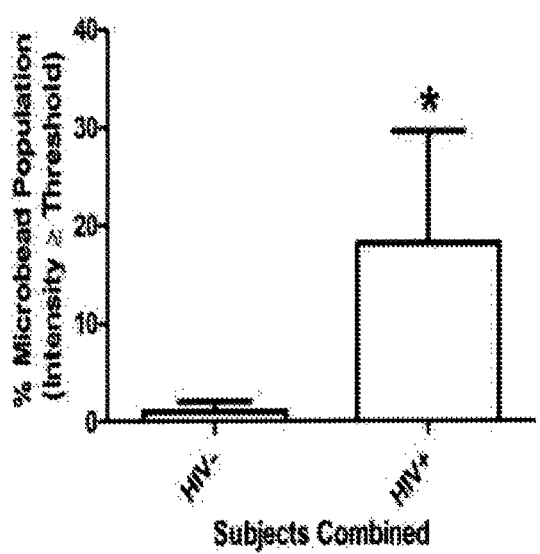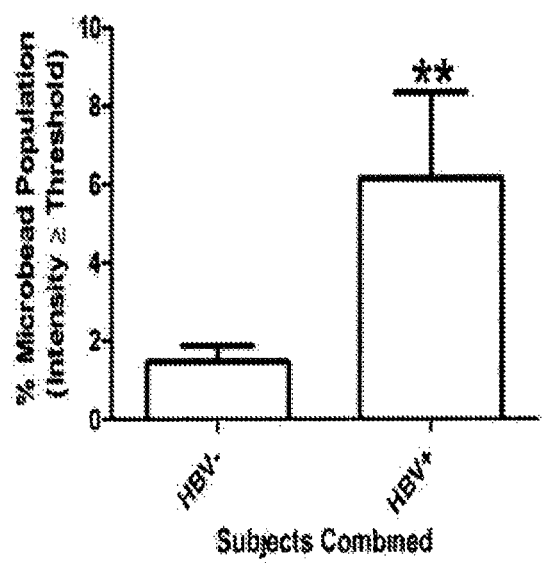
Fig. 9C    Fig. 9D

| Disease/ Biomarker | Capture Name/ Sequence (5' to 3') | Target/Amplicon Name and Sequence (5' to 3') | Secondary Probe Name/ Sequence | Corresponding Barcode | Corresponding Spectrum |
|---|---|---|---|---|---|
| Influenza Hemagglutinin – Influenza Type A (H1N1) | C_H1N1 CCC TCT TAG TTT GCA TAG TTT CCC GTT ATG (SEQ ID NO: 5) | T_H1N1 CGG CGA TGA ATA CCT AGC ACA CTT A CTA CA TAA CGG GAA ACT ATG CAA ACT AAG AGG G (SEQ ID NO: 6) | D 5'-Alexa647- TAA GTG TGC TAG GTA TTC ATC GCC G-3' (SEQ ID NO: 7) | B_H1N1  20 μm | |
| Influenza Neuraminidase – Influenza Type A (H3N2) | C_H3N2 ACT TGG TTG TTT GGG GGG GAG TTG AAT TCA (SEQ ID NO: 8) | T_H3N2 CGG CGA TGA ATA CCT AGC ACA CTT A CTA TG AAT TCA ACT CCC CCC CAA ACA ACC AAG T (SEQ ID NO: 9) | | B_H3N2  20 μm | |
| Influenza Hemagglutinin – Influenza Type A (H5N1) | C_H5N1 CCA TTC CCT GCC ATC CTC CCT CTA TAA AAC (SEQ ID NO: 10) | T_H5N1 CGG CGA TGA ATA CCT AGC ACA CTT A CTA GT TTT ATA GAG GGA GGA TGG CAG GGA ATG G (SEQ ID NO: 11) | | B_H5N1  20 μm | |

FIG. 10

| Disease/Biomarker | Capture Name/Sequence (5' to 3') | Target / Amplicon Name and Sequence (5' to 3') | Secondary Probe Name/Sequence | Corresponding Barcode | Corresponding Spectrum |
|---|---|---|---|---|---|
| Influenza<br><br>Influenza Type B | C_FluB<br><br>CAC CGC AGT TTC AGC TGC TCG AAT TGG (SEQ ID NO: 12) | T_FluB<br><br>CGG CGA TGA ATA CCT AGC ACA CTT A CTA CC AAT TCG AGC AGC TGA AAC TGC GGT G (SEQ ID NO: 13) | D<br><br>5'-Alexa647-TAA GTG TGC TAG GTA TTC ATC GCC G-3' (SEQ ID NO: 14) | 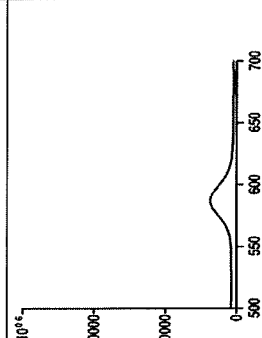 B_FluB | |
| Human Immuno-deficiency Virus (HIV)<br><br>SK102 HIV-1 | C_HIV<br><br>GAG ACC ATC AAT GAG GAA GCT GCA GAA TGG GAT (SEQ ID NO: 15) | T_HIV<br><br>CGG CGA TGA ATA CCT AGC ACA CTT A CTA AT CCC ATT CTG CAG CTT CCT CAT TGA TGG TCT C (SEQ ID NO: 16) | | 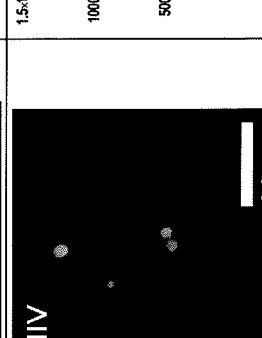 B_HIV | |
| Hepatitis B (HBV)<br><br>PB-2 – HBV | C_HBV<br><br>TCA GAA GGC AAA AAA GAG AGT AAC T (SEQ ID NO: 17) | T_HBV<br><br>CGG CGA TGA ATA CCT AGC ACA CTT A CTA AG TTA CTC TCT TTT TTG CCT TCT GA (SEQ ID NO: 18) | | 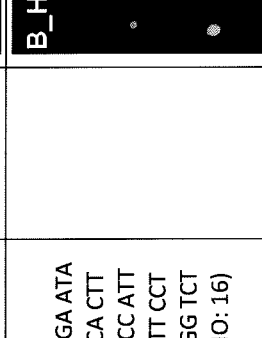 B_HBV | |

FIG. 10 (continued)

| Disease/ Biomarker | Capture Name/ Sequence (5' to 3') | Target / Amplicon Name and Sequence (5' to 3') | Secondary Probe Name/ Sequence | Corresponding Barcode | Corresponding Barcode Spectrum |
|---|---|---|---|---|---|
| Hepatitis C (HCV) KY 150 – HCV | C_HCV CAT AGT GGT CTG CGG AAC CGG TGA GT (SEQ ID NO: 19) | T_HCV CGG CGA TGA ATA CCT AGC ACA CTT A CTA AC TCA CCG GTT CCG CAG ACC ACT ATG (SEQ ID NO: 20) | D 5'-Alexa647- TAA GTG TGC TAG GTA TTC ATC GCC G- 3' (SEQ ID NO: 21) | B_HCV | |
| Positive Control | C_Pos GAC AAT GCT CAC TGA GGA TAG T (SEQ ID NO: 22) | T_Pos CGG CGA TGA ATA CCT AGC ACA CTT A CTA AC TAT CCT CAG TGA GCA TTG TC ((SEQ ID NO: 23) | | B_Pos | |
| Negative Control | C_Neg CCA ATA TCG GCG GCC ((SEQ ID NO: 24) | T_Neg CGG CGA TGA ATA CCT AGC ACA CTT A CTA GG CCG CCG ATA TTG G (SEQ ID NO: 25) | | B_Neg | |

FIG. 10 (continued)

| Disease/ Biomarker | Capture Name/ Sequence (5' to 3') | Target / Amplicon Name and Sequence (5' to 3') | Secondary Probe Name/ Sequence | Corresponding Barcode | Corresponding Barcode Spectrum |
|---|---|---|---|---|---|
| Clinical HIV Sample | CC_HIV GAA AGG TGA AGG GGC AGT AGT AAT ACA AGA C AAT AGT GAC ATA AAG GTA GTA CCA AGA AGA AAA GCA AAG ATC ATT AGG GAT TAT GGA AAA CAG ATG GCA GGT GAT GAT TGT GTG G (SEQ ID NO: 26) | CT_HIV TTT TTT TTT GCC ACA CAA TCA TCA CCT GCC ATC TGT TTT CCA TAA TCC CTA ATG ATC TTT GCT TTT (SEQ ID NO: 27) | CD_HIV 5'-Alexa647-TTG GTA CTA CCT TTA TGT CAC TAT TGT CTT GTA TTA CTA CTG CCC CTT CAC CTT TCC-3' (SEQ ID NO: 28) | 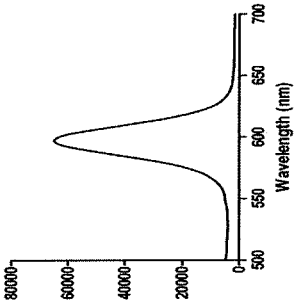 |  |

FIG. 10 (continued)

| Disease/ Biomarker | Capture Name/ Sequence (5' to 3') | Target / Amplicon Name and Sequence (5' to 3') | Secondary Probe Name/ Sequence | Corresponding Barcode | Corresponding Barcode Spectrum |
|---|---|---|---|---|---|
| Clinical HBV Sample | CC_HBV GGC ATG GAC ATT GAC CCT TAT AAA GAA TTT GGA GCT TCT GTG GAG TTA CTC TCT TTT TTG CCT TCT GAT TTC TTT CCG TCT ATT CGG GAC CTT CTC GAC A (SEQ ID NO: 29) | CT_HBV AAA AAA AAA TGT CGA GAA GGT CCC GAA TAG ACG GAA AGA AAT CAG AAG GCA AAA AA (SEQ ID NO: 30) | CD_HBV 5'-AAC TCC ACA GAA GCT CCA AAT TCT TTA TAA GGG TCA ATG TCC ATG CC-Alexa647-3' (SEQ ID NO: 31) | 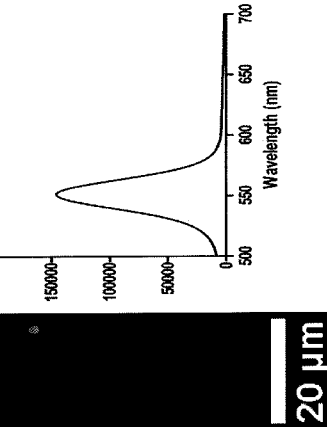 | |

FIG. 10 (continued)

| Disease/ Biomarker | Capture Name/ Sequence (5' to 3') | Target / Amplicon Name and Sequence (5' to 3') | Secondary Probe Name/ Sequence | Corresponding Barcode | Corresponding Barcode Spectrum |
|---|---|---|---|---|---|
| Clinical Positive Control | CC_Pos GAC AAT GCT CAC TGA GGA TAG T (SEQ ID NO : 32) | CT_Pos CGG CGA TGA ATA CCT AGC ACA CTT A CTA AC TAT CCT CAG TGA GCA TTG TC (SEQ ID NO : 33) | CD 5'-Alexa647-TAA GTG TGC TAG GTA TTC ATC GCC G-3' (SEQ ID NO : 34) | CB_Pos 20 μm | |
| Clinical Negative Control | CC_Neg CCA ATA TCG GCG GCC (SEQ ID NO: 35) | CT_Neg CGG CGA TGA ATA CCT AGC ACA CTT A CTA GG CCG CCG ATA TTG G (SEQ ID NO: 36) | | CB_Neg 20 μm | |

FIG. 10 (continued)

AMPLIFICATION OF NANOPARTICLE BASED ASSAY

CROSS REFERENCE TO RELATED APPLICATIONS

This application claims the benefit of U.S. Provisional Ser. No. 62/181,907, filed Jun. 19, 2015, the contents of which are hereby incorporated by reference into the present disclosure.

REFERENCE TO SEQUENCE LISTING SUBMITTED VIA EFS-WEB

This includes an electronically submitted sequence listing in .txt format. The .txt file contains a sequence listing entitled "2021-9-8 58185-400 Sequence listing_ST25.txt" created on Sep. 8, 2021 and is 8 kilobytes in size. The sequence listing contained in this .txt file is part of the specification and is hereby incorporated by reference herein in its entirety.

FIELD OF THE INVENTION

The present disclosure relates to invention of integrating an isothermal amplification step to enhance the signal generated from a target molecule for assays that involve the use of metal-containing nanoparticles.

BACKGROUND OF THE INVENTION

Most of widespread infectious diseases in developing countries may be treatable if addressed with proper therapy or medication at the early stage of infection; nonetheless, the identification of infected patients for rapid response to the disease remains a major challenge in the field [Mabey, D.; Peeling, R. W.; Ustianowski, A.; Perkins, M. D. Diagnostics for the developing world. Nat Rev Micro 2004, 2, 231-240]. Consequently, there is an increasing demand for cost-effective and portable point of-care (POC) diagnostic device [Hauck, T. S.; Giri, S.; Gao, Y.; Chan, W. C. W. Nanotechnology diagnostics for infectious diseases prevalent in developing countries. Advanced Drug Delivery Reviews 2010, 62, 438-448]. Ultimately, such a diagnostic device should be ease-to-use and detect multiple infectious agents with high sensitivity and specificity for it to be applicable in resource-poor settings.

Nanoparticles are important components in many diagnostic and detection systems. These nanoparticles may possess unique properties that enable them detect biological molecules in both patient and non-patient samples. However, nanoparticle detection system, especially for detecting genomic materials, have limited sensitivity and therefore, these technologies may not be useful in the real world. The sensitivity of conventional QD barcode assay is not high enough to detect many infections that have low-abundance target analytes and stringent detection limit specifications, and current DNA extraction procedures highly depend on manual and laborious sample processing. For example, current quantum dot barcode system technology for detecting HIV, hepatitis B, hepatitis C, is limited for properly diagnosing patients because the technology can only detect 1 femtomole (10-15 mol of the DNA target). Considering that many of these nanoparticle detection systems will be used at point-of-care, the nanoparticle-based assay will always measure a negative detection, but such measurements will not be accurate. There is a need, therefore, to develop a diagnostic system that can easily detect genomic materials from clinical samples and achieve highly reliable clinical sensitivity and specificity for POC testing.

Detection of genomic material such as DNA as biomarkers is currently a widely used technique for pathogenic detection. Polymerase chain reaction (PCR) is one of the most common techniques used in current infectious disease diagnostic tests. PCR, however, is not well suited for use in POC settings due to the use of an expensive thermal cycler, and also trained technicians are needed to operate the test [Hauck et al. Adv. Drug Delivery Reviews, 62, 438-448, 2009]. As a result, there is an increasing demand for developing PCR-less amplification strategies, which can effectively enrich the amount of target DNA and which can effectively and synergistically co-operate with naoparticle-based technologies.

Isolation of genomic material from a crude sample is an important step involved in molecular biology. Traditional DNA extraction methods using phenolchloroform or spin columns are difficult to scale-down sample volumes, time consuming, laborious and hard to automate making them not suitable for POC applications [Berensmeier, S. Magnetic particles for the separation and purification of nucleic acids. Appl Microbiol Biotechnol 2006, 73, 495-504; Chung, Y.-C.; Jan, M. S.; Lin, Y.-C.; Lin, J.-H.; Cheng, W.-C.; Fan, C.-Y. Microfluidic chip for high efficiency DNA extraction. Lab Chip 2004, 4, 141]. Many studies have investigated using a microfluidic device combined with either magnetic beads or immiscible organic phase to automate the extraction of nucleic acids, and demonstrated the potential for parallelizing experiments while reducing the operational complexity and cost [Breadmore, M. C.; Wolfe, K. A.; Arcibal, I. G.; Leung, W. K.; Dickson, D.; Giordano, B. C.; Power, M. E.; Ferrance, J. P.; Feldman, S. H.; Norris, P. M.; Landers, J. P. Microchip-Based Purification of DNA from Biological Samples. Anal. Chem. 2003, 75, 1880-1886; Zhang, R.; Gong, H.-Q.; Zeng, X.; Lou, C.; Sze, C. A Microfluidic Liquid Phase Nucleic Acid Purification Chip to Selectively Isolate DNA or RNA from Low Copy/Single Bacterial Cells in Minute Sample Volume Followed by Direct On-Chip Quantitative PCR Assay. Anal. Chem. 2013, 85, 1484-1491]. Nonetheless, these devices relied on using syringe pumps to pass fluids through the microfluidic channels, which is not desirable in POC settings due to limited availability of the instruments. Therefore, there is a demand for technology that can automate DNA extraction, DNA amplification and multiplex detection of the amplified DNA that can be used for POC applications.

A microfluidic device has been developed to automate the assay [Gao, Y.; Lam, A. W. Y.; Chan, W. C. W. Automating Quantum Dot Barcode Assays Using Microfluidics and Magnetism for the Development of a Point-of-Care Device. ACS Appl. Mater. Interfaces 2013, 5, 2853-2860]. This device achieved a detection limit of 1.2 nM, and demonstrated multiplexed detection of genetic biomarkers for HIV, HBV and syphilis diseases. Although this device demonstrated automation of the assay, it does not include an automated sample pretreatment for DNA extraction and amplification.

SUMMARY OF THE INVENTION

The present invention relates to a nanoparticle-based multiplex diagnostic systems and methods. The nanoparticle-based multiplex diagnostic systems and methods of the present invention overcome the low sensitivity of microbead-based hybridization assays by including a genomic material amplification compartment or step that enables the systems and methods of the present invention for use at point-of-care (POC) settings.

As such, in an embodiment, the present invention provides for an automated multiplex detector system, the system including: (a) a nucleic acid amplification compartment for amplifying nucleic acid of one or more targets in a sample, and (b) an analysis compartment in communication with the amplification compartment, the analysis compartment housing a nanoparticle-based multiplex detector configured for receiving the amplified nucleic acid of the amplification compartment and producing a signal that correlates the amplified nucleic acid with the presence of the one or more targets in the sample.

In one embodiment of the system of the present invention, the system further includes (c) a nucleic acid extraction compartment in communication with the amplification compartment for delivering extracted nucleic acid to the amplification compartment, and (d) a reagent storage compartment in communication with the extraction and amplification compartments for delivering reagents to the extraction and amplification compartments.

In another embodiment of the system of the present invention, wherein the nucleic acid amplification compartment includes one or more amplification reaction channels and amplification reagent delivery inlets extending from the amplification reaction channels, the amplification delivery inlets in communication with the reagent storage compartment for delivering nucleic acid amplification reagents to the amplification reaction channel.

In another embodiment of the system of the present invention, the amplification reagents are reagents necessary for an isothermal recombinase polymerase amplification assay.

In another embodiment of the system of the present invention, the nucleic acid extraction compartment includes a main channel, one or more extraction reagent delivery inlets connecting the reagent storage compartment with the main channel for sequentially delivering extraction reagents to the main channel, and one or more permanent magnets distributed along the main channel.

In another embodiment of the system of the present invention, the extraction reagents delivery inlets include a sample delivery inlet, a lysis buffer inlet, a magnetic beads and binding buffer inlet, a washing buffer inlet and an elution buffer inlet.

In another embodiment of the system of the present invention, the main extraction channel includes: (a) a lysis zone in communication with the lysis and sample inlets, (b) a binding zone in communication with the magnetic beads and binding buffer inlet, the binding zone being separated from the lysis zone by a first gate, (c) a washing zone in communication with the washing buffer inlet, (d) an elution zone in communication with the elution buffer inlet, (e) a first outlet extending for releasing extracted nucleic acid, (f) a second outlet for releasing waste, the second outlet being separated from the main extraction channel by a second gate.

In another embodiment of the system of the present invention, the system includes two or more permanent magnets distributed along the main channel for directing the magnetic beads to the elution zone.

In another embodiment of the system of the present invention, the nanoparticle in any of the previous embodiments is selected from the group consisting of: metal, semiconductor or organic based nanostructures or molecules, organic dyes, or a combination thereof.

In another embodiment of the system of the present invention, the nanoparticle-based multiplex detector in any of the previous embodiments includes a quantum dot barcode assay.

In another embodiment of the system of the present invention, the nanoparticle-based multiplex detector in any of the previous embodiments includes a multicomponent nucleic acid enzyme (MNAzyme) based gold nanoparticle (GNP) assay.

In another embodiment of the system of the present invention, the signal in any of the previous embodiments is a quantifiable color or fluorescence signal of the amplified nucleic acid.

In another embodiment of the system of the present invention, the system of any of the previous embodiments further includes a wireless communication device configured for relaying the signal of the amplified nucleic acid.

In another embodiment of the system of the present invention, the reagents referred to in any of the previous embodiments, are stored in the reagent storage compartment in solution, lyophilized or powder form.

In another embodiment, the present invention relates to a method for simultaneously detecting the presence or absence of one or more targets of interest in a sample, the method including: (a) providing an automated multiplex detector system according to any of the previous embodiments, (b) amplifying the nucleic acid of the one or more targets in the sample in the amplification compartment of the system, (c) contacting the amplified nucleic acid with the nanoparticle-based multiplex detector to generate the signal, and (d) correlating the signal of the amplified nucleic acid with the presence or absence of the one or more targets of interest in the sample.

In one embodiment of the method of the present invention, the system includes the nucleic acid extraction compartment in communication with the amplification compartment, and wherein prior to the amplification step (b), the method includes extracting the nucleic acid of the one or more targets in the sample and delivering the extracted to the amplification compartment.

In one embodiment of the method of the present invention, the amplification of the nucleic acid of step (b) is an isothermal recombinase polymerase amplification assay.

In another embodiment of the method of the present invention, the multiplex detector includes different populations of primary probes having nanoparticles and secondary probes, each population corresponding to one specific target, the primary and secondary probe of each population having a ligand that binds to nucleic acid characteristic of the population's target, such as in the presence of the nucleic acid of the population's target a complex is formed between the primary probe, the secondary probe and the nucleic acid of said target, the complex generating two signals, a first signal emitted from the first probe which distinguishes the identity of the population's target, and a second signal emitted from the second probe which identifies the presence or absence of the population's target, and the method further comprises (c) exciting the different populations of primary and secondary probes to generate corresponding first and second signals; and (d) reading the first and second signals from the populations of primary and secondary labels, whereby the presence of a first and second signal in one population is indicative of the identity and presence of said population's target in the sample.

In another embodiment of the method of the present invention, the multiplex detector comprises (i) a nucleic acid substrate, (ii) a pre-catalytic nucleic acid subunit, the pre-catalytic nucleic acid subunit including a sensor domain configured for binding to at least a portion of the biological target, and a catalytic domain which catalyzes the nucleic acid substrate solely when the target is bound to the sensor domain, and (iii) gold nanoparticles (GNPs), the GNPs functionalized with a linking moiety for crosslinking with the nucleic acid substrate in the absence of the target; and (b) optically analyzing the sample to determine whether the GNPs substantially crosslinked with the nucleic acid substrate, wherein when crosslinked with the nucleic acid substrate the GNPs turn the sample to a first color, and in the presence of the target, GNPs turn the sample to a second color indicative that the target is present in the sample.

In another embodiment of the method for simultaneously detecting the presence or absence of one or more targets of interest in a sample of the present invention, the method of any of the previous embodiments uses a system according to any of the automated multiplex detector systems described above.

In another embodiment of the present invention, the communication referred to above in any of the previous system or method embodiments, is fluid communication.

BRIEF DESCRIPTION OF THE DRAWINGS

Embodiments will now be described, by way of example only, with reference to the drawings, in which:

FIG. 1A: A visual representation of a device in accordance to one embodiment of the present invention, with the different compartments colored for clarity, capillary tubes to show the flow of solutions between them, and a smartphone for scale. FIG. 1B Schematics of the device of panel 1A with colors matching the various compartments in 1A and numbers indicating the movement of sample in these compartments. FIG. 1C A flow diagram illustrating the steps in a method for detecting pathogen targets using the device of the present invention, from patient sample to imaging and analysis, with colors and numbers matching the compartments in FIGS. 1A and 1B. The liquid can be moved from one compartment to the next using electrically-driven flow.

FIG. 6A) are compared with quantum dot barcodes ('QD540' and 'QD640';

FIG. 6B): excitation/absorption and emission spectra; visual images captured by our device when excited using a 405 nm laser excitation source; emission spectra under varying excitation wavelengths; and photobleaching under continuous excitation in the device, representing the average intensities of 591, 642, 1198, and 1145 barcodes analyzed, over the 180 s duration, for 'Yellow', 'Nile Blue', 'QD540', and 'QD640', respectively.

FIG. 7A Microphotograph illustrating yellow, green, and red barcodes (identified as B_HBV, B_HCV, and B_Pos in Table 1, respectively) which were deposited on the chip and imaged using the device ($\lambda ex=405$ nm, $\lambda em=430LP$, exposure time=1 s). Arrows point to yellow barcodes. FIG. 7B After the assay, the device-acquired fluorescence image of the microbeads bound with the target analyte and secondary probe ($\lambda ex=655/15$, $\lambda em=692/40$, exposure time=1 s). Both green and red microbeads had positive signals. This demonstrates that their respective genomic targets are present in the sample but not for the yellow barcode as shown by the arrows. FIG. 7C Sensitivity curves for genetic biomarkers for the bloodborne viruses human immunodeficiency virus (HIV), hepatitis B virus (HBV) and hepatitis C virus (HCV), representing 8017, 7324, 10334 barcodes analyzed, respectively. FIG. 7D Sensitivity curves for genetic biomarkers for the influenza A viruses H1N1, H3N5, and H5N1; influenza B virus (FluB), representing 8491, 5967, 10182, and 4114 barcodes analyzed, respectively. All values represent the average secondary probe intensity, and error bars were calculated based on the standard deviation from three replications of each condition.

FIGS. 8A to 8F are bar graphs illustrating multiplexed detection for synthetic target strands for the bloodborne viruses HIV, HBV, HCV with positive and negative controls. FIG. 8A Only positive control was present during hybridization, representing 1039 barcodes analyzed. FIG. 8B Targets for HIV and positive control were present during hybridization, representing 1581 barcodes analyzed. FIG. 8C Targets for HBV and positive control were present during hybridization, representing 1749 barcodes analyzed. FIG. 8D Targets for HCV and positive control were present during hybridization, representing 1202 barcodes analyzed. FIG. 8E Targets for HIV, HBV, and positive control were present during hybridization, representing 2401 barcodes analyzed. FIG. 8F All targets except for negative control were present during hybridization, representing 1343 barcodes analyzed. Results represent data from three experimental replications of each condition combined into a single data set. Note that samples above the dashed 30% line are considered positive detection, otherwise they are considered negative detection.

FIGS. 9A to 9H are graphs illustrating detection of HIV and HBV in patient samples. FIG. 9A Detection of mono-infected amplified samples from 3 healthy subjects and 10 HIV positive patients, representing 1306, 728, 650 321, 1573, 626, 297, 1268, 429, 468, 499, 332, 375, and 287 barcodes analyzed, respectively, for each subject. FIG. 9B Detection of mono-infected amplified samples from 3 healthy subjects and 7 HBV positive patients, representing 361, 207, 1345, 371, 221, 1310, 806, 665, 778, and 674 barcodes analyzed, respectively, for each subject. FIG. 9C Comparison between the average combined statistics of all subjects of the healthy group (3 subjects) and HIV positive patients (10 subjects) from (a); error bars represent standard deviation, with statistical significance (P<0.05) indicated and determined using two-sided t-test. FIG. 9D Comparison between the average combined statistics of all subjects of the healthy group (3 subjects) and HBV positive patients (7 subjects) from FIG. 9B; error bars represent standard deviation, with statistical significance (P<0.01) indicated and determined using two-sided t-test. FIGS. 9E to 9H Detection of co-infection assays simulated with amplified healthy, HIV, and HBV positive patient samples. FIG. 9E Only positive control was present during hybridization, representing 384 barcodes analyzed. FIG. 9F HIV patient sample and positive control was present during hybridization, representing 866 barcodes analyzed. FIG. 9G HBV patient sample and positive control was present during hybridization, representing 1888 barcodes analyzed. FIG. 9H HIV and HBV patient samples, and positive control, were present during hybridization, representing 1019 barcodes analyzed. Results represent data from three replications of each condition combined into a single data set. Note that samples above the dashed 3% line are considered positive detection, otherwise they are considered negative detection. All samples were amplified. Additionally, all samples were blinded during the experiment to reduce bias.

FIG. 10 is a table listing DNA sequences and their corresponding barcode images and the corresponding barcode spectra.

FIG. 13 HPV-16 RPA products visualized on 3% agarose gel electrophoresis (135V, 30 minutes).

FIG. 14 QD barcode assay conducted with HPV-16 RPA amplicons produced in FIG. 13B FIG. 14A Detection probe signals (FL4) measured by flow cytometry.

DETAILED DESCRIPTION OF THE INVENTION

Figure 2:
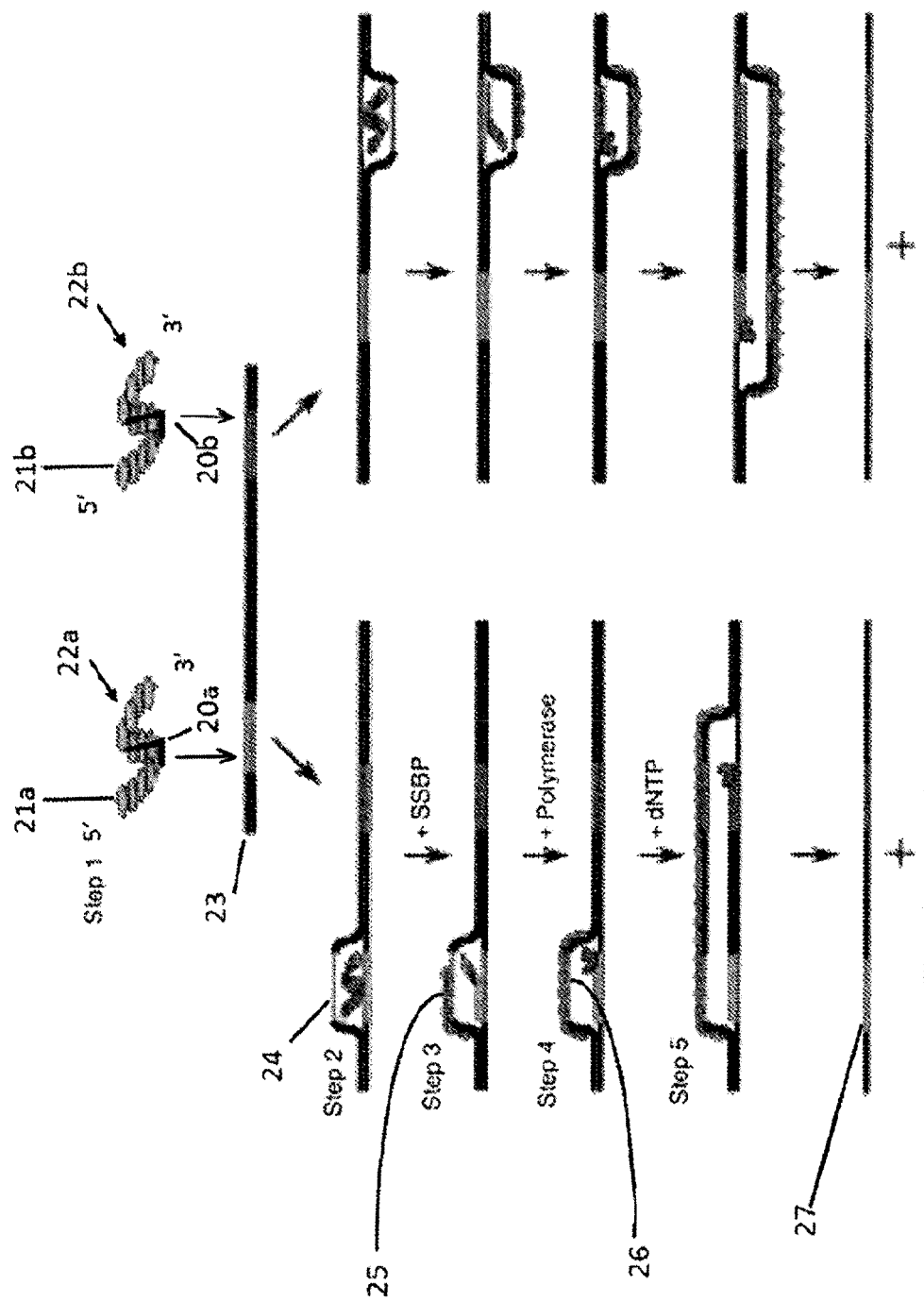
FIG. 2 is a schematic of an isothermic recombinase polymerase amplification sequence.

In this specification and in the claims that follow, reference will be made to a number of terms that shall be defined to have the meanings below. All numerical designations, e.g., dimensions and weight, including ranges, are approximations that typically may be varied (+) or (−) by increments of 0.1, 1.0, or 10.0, as appropriate. All numerical designations may be understood as preceded by the term "about".

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. The use of "/" means "and/or." Non-limiting terms are not to be construed as limiting unless expressly stated or the context clearly indicates otherwise (for example "including", "having" and "comprising" typically indicate "including without limitation"). "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention. Singular forms including in the claims such as "a", "an" and "the" include the plural reference unless expressly stated otherwise. In order to aid in the understanding and preparation of the within invention, the following illustrative, non-limiting, examples are provided.

"GNP" or "GNPs" refer to gold nanoparticle(s).

The term "ligand" or "capture molecule" as used herein refers to a molecule, organic or inorganic, or group of molecules that exhibits selective and/or specific binding to one or more organic or inorganic targets. Targets may include specific sites of a receptor, a probe, another molecule (organic or inorganic) or target or whole microscopic organisms (unicellular or multicellular) such as a pathogen. There can exist more than one ligand for a given target. The ligands may differ from one another in their binding affinities for the target. Examples of ligands include nucleotide-based ligands (aptamers, oligonucleotides, and so forth), amino acid-based ligands (antibodies, peptides, proteins, enzymes, receptors and so forth), polysaccharide-based ligands (for example hyaluronan), antigens, hormones, including peptide-hormones, lipid/phospholipid-hormones and monoamine hormones, and any other molecule capable of binding to an organic or inorganic target.

"Multiplex" may be understood as the ability to detect the presence of more than one target simultaneously. The multiplex detection system may include barcodes, metal, semiconductor, or organic based nanostructures or molecules, (e.g. organic dyes) or multicomponent nucleic acid enzyme (MNAzyme) based gold nanoparticle (GNP) systems.

Barcodes may include any type of structure or system that allows a target to be distinguished. Barcodes that may be used with the present invention include magnetic, optical (i.e. quantum dots, organic dyes), electrical, DNA and Lithographic barcodes.

"Probe" refers to a molecule or group of molecules used to study the presence or absence of analytes or targets in a sample. The probe has a measurable property that changes when it interacts, or not, with the analyte or target. Examples of probes used in this invention include quantum dot barcodes, fluorophores such as Alexa Fluor 647, quantum dots, metal nanoparticles, upconverting nanoparticles and so forth.

As used herein, a "quantum dot" (QD) is a semiconducting photoluminescent material, as is known in the art (for example, see Alivasatos, Science 271:933-937 (1996)). Non-limiting examples of QDs include: CdS quantum dots, CdSe quantum dots, CdSe/CdS core/shell quantum dots, CdSe/ZnS core/shell quantum dots, CdTe quantum dots, PbS quantum dots, and/or PbSe quantum dots. As is known to those of skill in the art, CdSe/ZnS means that a ZnS shell is coated on a CdSe core surface (ie: "core-shell" quantum dots). The shell materials of core-shell QDs have a higher bandgap and passivate the core QDs surfaces, resulting in higher quantum yield and higher stability and wider applications than core QDs.

Quantum dot barcodes refers to microbeads containing different combinations of fluorescent semiconductor nanocrystals. Each microbead may include a unique optical signature that identifies a surface conjugated molecule. Approximately 10,000 to 40,000 different optical barcodes may be engineered using 5-6 different color quantum dots and six intensity levels [11]. This enables significant multiplexing and these barcodes can detect targets in a flow cytometer [1, 2, 12, 13] or microfluidic channel [3, 5] as well as through other means.

"Target" or refers to a biological target, including, infectious and non-infectious organisms.

Wireless communication device refers to any device using radio-frequency, infrared, microwave, or other types of electromagnetic or acoustic waves in place of wires, cables, or fibre optics to transmit or receive signals or data, and that the device includes a camera for acquiring images, signals or data and electronic components to sustain analysis of the images, signals or data. Wireless communication devices include smart phones, tablets, smart watches, personal assistant devices, and portable computers.

The present invention demonstrates that the integration of a genomic material amplification step may be used in a system for multiplex detection and identification of targets of interest at the point of care (POC).

Figure 4:
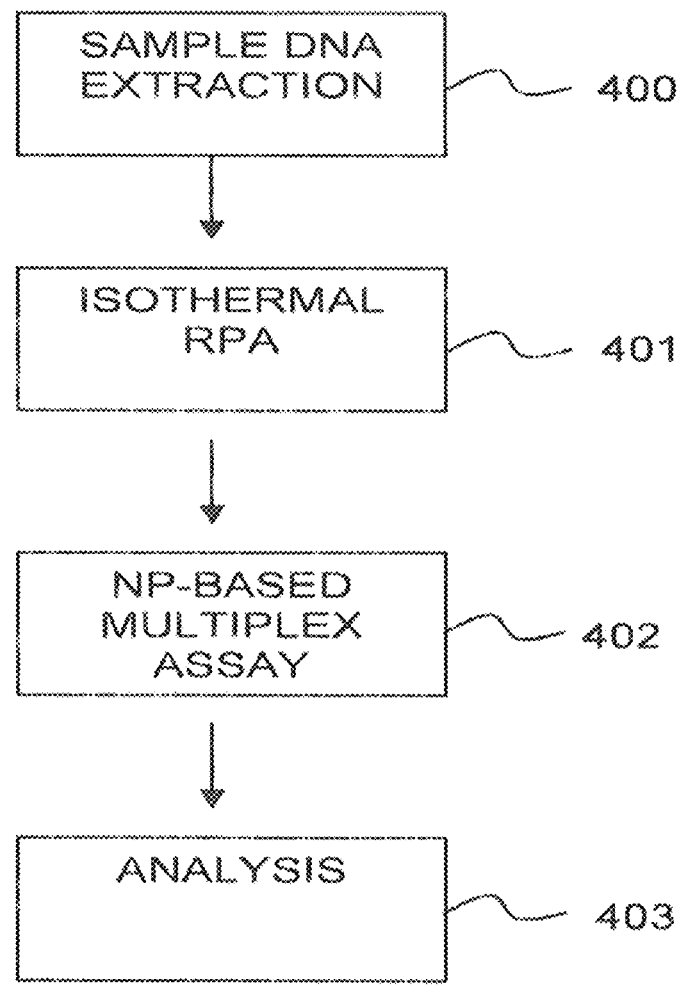
FIG. 4 is flow char illustrating a multiplex detection method in accordance to one embodiment of the present invention.

As shown in FIG. 1C (for convenience, the compartments of the device of FIG. 1B which carry out the steps of FIG. 1C carry the same number, but in the steps the numbers are followed by "s"), the steps in the POC methods of the present invention include at least (1) amplification of the target 1s, (2) recognition and hybridization of the target to barcodes (primary probe) on chip 3s and to secondary probes, and (3) read-out of the chip signal 4s with a suitable device, such as a wireless communication device 9 as shown in FIG. 1a. Primary probes refers to molecules that recognize adsorbed and conjugated biorecognition molecule and secondary probes are probes that recognize the primary probe. The steps in the method may also include the extraction of the genetic material of the target 2s. The steps may also include sample collection 12s and display of results 13s. With these current steps, a device 10 with specific chambers for each of these steps is herein provided (FIG. 1A and FIG. 1B). Each chamber or compartment in the device 10 may contain disposable lyophilized or powder reagents that may be dissolved by buffers, and transferred from one compartment to the next using capillaries 11, which may also be referred to as inlets, and electrically-driven flow. The device may also be custom-designed for different types of target molecules. For example, in detection of a protein target, the extraction and amplification steps may not be needed. The number of chambers in the device may be engineered according to the target molecule and may include less or more chambers than those shown in FIG. 1B. In FIG. 1B the following chambers or compartments are shown: extraction compartment 1, such as extraction of DNA, amplification compartment 2, such as DNA amplification, on-chip assay compartment 3 (an example is illustrated in FIG. 4), imaging and analysis compartment 4, buffer/reagent compartments 5, which may include sub compartments for amplification buffers/reagents, binding buffers/reagents, elution buffers/reagents, washing buffers/reagents, lysis buffers/reagents and so forth) power compartment 6, heating and pump controls compartment 7 and waste compartment 8.

The Amplification Step

Incorporating an amplification technique that is compatible with multiplex detection system and that can be used at a POC is not trivial or obvious to one of ordinary skill in the art. The applicant unexpectedly discovered that an isothermal nucleic acid amplification technique, recombinase polymerase amplification (RPA), may be used with the multiplex detection systems of the present invention. This amplification technique was shown to achieve an exponential nucleic acid amplification at a low constant temperature (about 37 deg C.) without the initial thermal denaturation [Piepenburg, O.; Williams, C. H.; Stemple, D. L.; Armes, N. A. DNA Detection Using Recombination Proteins. Plos Biol 2006, 4, e2041. There are five main steps involved in this isothermal technique as illustrated in FIG. 2. In a first step, in the presence of ATP, recombinase proteins 21a,b (T4 UvsX) bind to forward 20a and reverse 20b primers to form nucleoprotein complex 22a,b, which, in step 2, then scan along double-stranded template DNA 23 to facilitate strand-exchange at the homologous sequence to form a D-loop structure 24. In step 3, single-stranded binding proteins (SSBP) 25 then bind to the displaced strand of template DNA and stabilize the resulting structure. As ATP gets hydrolyzed, nucleoprotein complex disassembles, and in step 4 polymerase 26 binds to 3'-end of primers 20a,b. Lastly in step 5, polymerase 26 adds dNTPs to 3'-end of primers 20a,b to synthesize DNA sequence 27 that is complementary to template DNA 23. This process may be repeated to achieve an exponential amplification until all primers in a pool of primers get depleted.

Genomic Material Extraction

Superparamagnetic nanoparticle-based extraction techniques have unique properties that may be exploited for the device of the present invention.

Currently, there are many commercially available magnetic beads for DNA extraction including Dynabeads® from Invitrogen, GenoPrep™ DNA magnetic beads from GenoVision, and MagneSil® from Promega, and these commercial kits share very similar working principle. In this isolation technique the crude sample is first lysed and mixed with magnetic beads and binding buffer. DNA binds to the surface of magnetic beads by electrostatic interaction or hydrogen bonding, and a permanent magnet is applied to localize the beads. After the addition of washing buffer, the supernatant is removed to discard contaminants, and elution buffer is added to release DNA from the magnetic beads. Lastly, a permanent magnet is applied again to immobilize beads and pure DNA can be collected from the solution [Berensmeier, S. Magnetic particles for the separation and purification of nucleicacids. Appl Microbiol Biotechnol 2006, 73, 495-504].

Magnetic bead technology offers a promising possibility for automation of DNA extraction, which is a step required for POC testing, where there's limited access to laboratory instruments, and for processing a large number of samples without repetitive pipetting steps while avoiding potential human errors. Many companies have invested and commercialized automated devices (Ex. KingFisher®96 from Thermo Labsystems and Maxwell™ 16 from Promega); however, these products are still bulky and require electric power; hence, they are mostly used in a centralized laboratory. A miniaturized microfluidic device has the potential to overcome this challenge by delivering a portable and automated POC DNA extraction system while reducing reagent cost and processing time.

Figure 3:
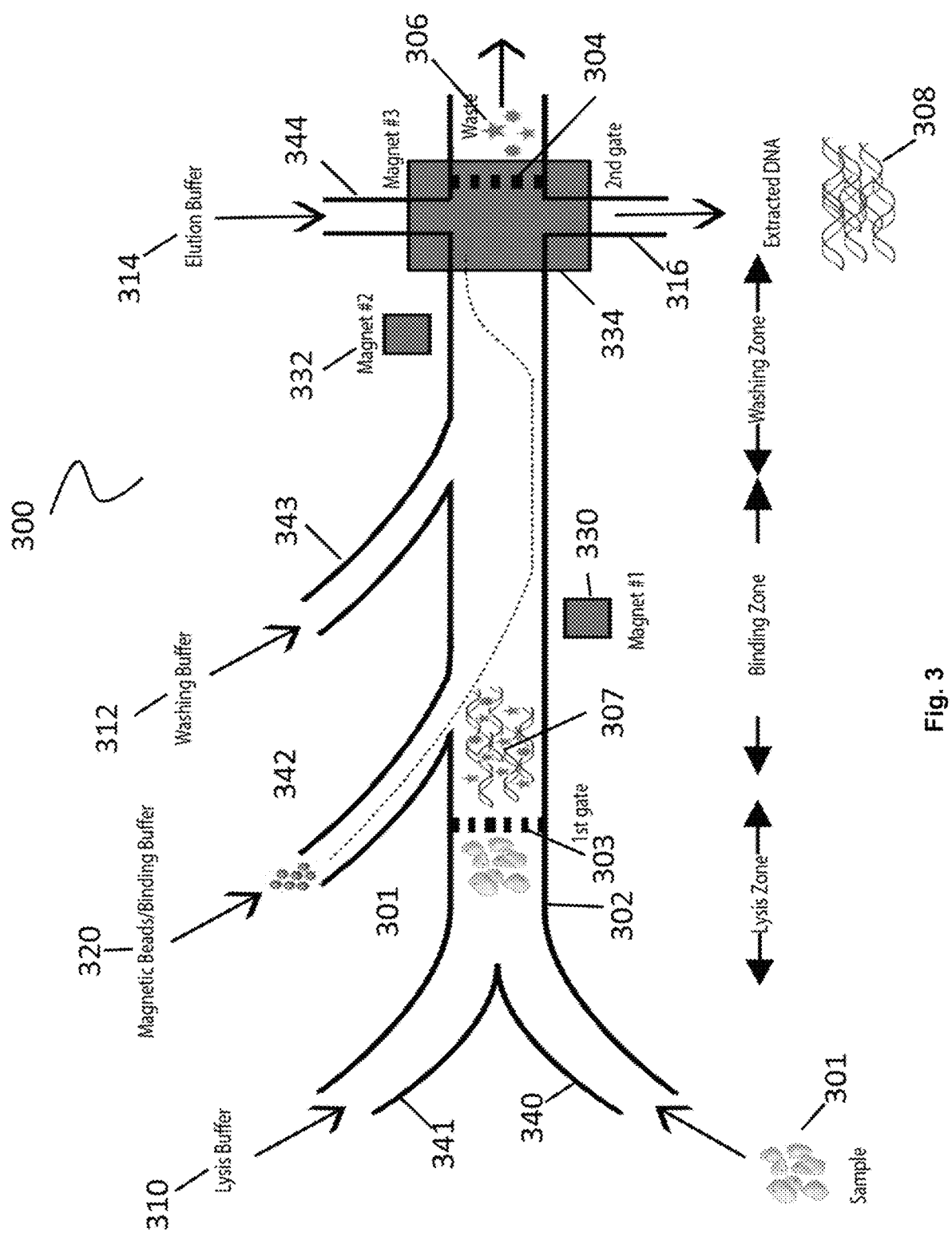
FIG. 3 is a schematic of genomic material extraction microfluidic device in accordance to one embodiment of the present invention.

A device 300 may be fabricated to automate DNA extraction from cells, such as cervical cells, bacteria and other infected cells such as epidermal cells as exemplified in FIG. 3. Crude sample 301 may be first injected to a main extraction channel 302, where it may be stopped by a first gate 303. Lysis buffer/reagent 310 may be added to disrupt the cell membrane of the sample 301, which will release cellular components 305 to pass through the first gate 303. Magnetic beads 320 together with binding buffer/reagent may be added along the channel, which will electrostatically bind DNA from cell lysate to form a magnetic bead/DNA complex and the complex is collected at the second gate 304. Washing buffer/reagent 312 may be added to remove waste or contaminants 306, and elution buffer/reagent 314 may be added to release DNA from magnetic beads 320. The chip dimensions and location of the magnets may be designed to achieve optimized reaction between magnetic beads and cell lysate. Lastly, the extraction efficiency of the automated device may be assessed by quantitative PCR and compared with manual extraction kits. The reagents may be provided as reagents in liophylized or powder into the main channel.

The reagents or buffers may be delivered to the main channel 302 through inlets, such as lysis inlet 341, sample inlet 340, magnetic beads/binding buffer inlet 342, washing buffer inlet 343, and elution buffer inlet 344. The inlets and channels may be provided, in one embodiment, in micrometer-size.

Multiplex Detector

The multiplex detector may be a nanoparticle based mutiplex system that is compatible with an isothermal amplification step and vice versa.

Figure 5A:
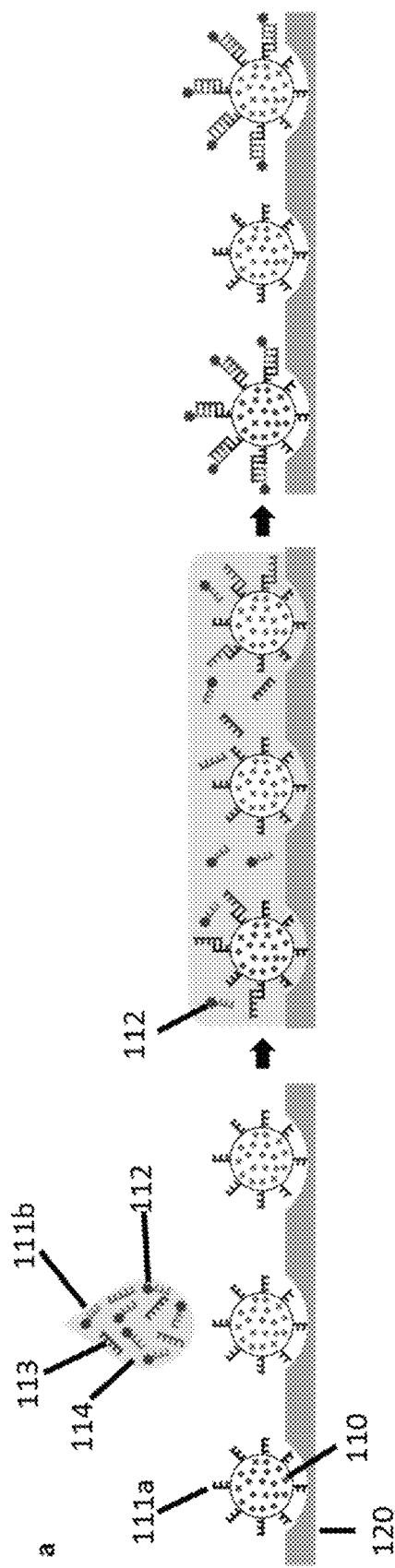
FIG. 5A Graph illustrating an embodiment of the method of the present invention which involves the addition of amplified nucleic acid patient samples to a chip coated with beads, which are optically barcoded by quantum dots and are coated with molecules that recognize a target analyte. This target analyte joins the barcode to the secondary probe. Since each barcode is conjugated with a known bio-recognition molecule for a specific pathogen target, the imaging of the optical signal from the barcode would allow for the identification of the pathogen and whether it is present in a patient sample (i.e. lack of secondary probe signal indicates no pathogen present, in this case the yellow bead).

With reference to FIG. 5A, in one embodiment, the multiplex detector may include a substrate 120. As illustrated in FIG. 5A the multiplex detection system may include a primary probe 110, a secondary probe 112, a capture ligand 111a to a target of interest coupled to the primary probe 110 and a detection ligand 111b to the target of interest coupled to the secondary probe 112. The secondary probe, such as a fluorophore, may be coupled to the same target-specific ligand as the one bound to the primary probe, or to another target-specific ligand. In FIG. 5A, the primary probe 110 is represented as quantum dot barcodes. It should be understood that other multiplexing systems may be used and that primary probes other than QD barcodes may be used. In a typical QD barcode assay, target biomarkers, such as target DNA 113 in an amplified patient sample solution 114 bind to capture ligands 111a and 111b whereby a complex is formed between the primary probe, the target and the secondary probe. There are two optical signals generated from this complex. The first signal is emitted from the primary probes, such as from QDs embedded inside microbeads, which distinguishes the identity of biomarker present in the sample. The second signal is generated from secondary probes, which identifies the presence or absence of the target. The secondary probe may be fluorophores but they can also be based on Raman signatures or color-based.

Figure 5B:
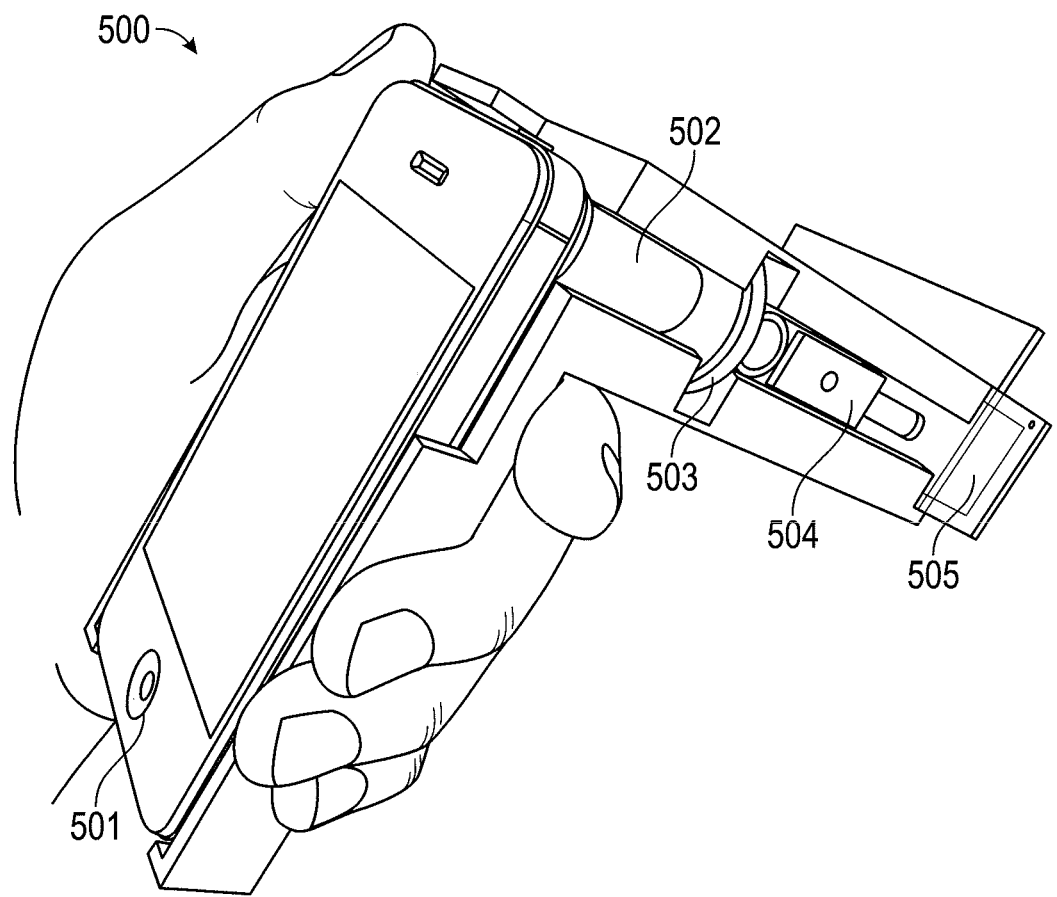
FIG. 5B Illustration of a smartphone point of care device in accordance to one embodiment of the present invention.

The device may also include an excitation source for exciting the primary probe and secondary probe, an optical means having an objective for collecting the optical emission from the excited primary label and secondary label, one or more filters for filtering the beams from the excitation source and the emissions from the primary label and secondary label. The device or system may also include a centralized facility for wirelessly receiving the data collected by the wireless communication device for storing or further analyzing the data collected. FIG. 5B illustrates system 500 in accordance to one embodiment of the present invention, having a wireless device 501, an eyepiece 502, emission filter 503, objectives 504 and a microwell chip 505.

Method

One embodiment of the multiplex detection method of the present invention is shown in FIG. 4. A first step 400 may involve extracting genetic material, such as DNA, of clinical samples. Microfluidic system of the present invention may be used to extract DNA of clinical samples. The extracted material may then be amplified in amplification step 401 using isothermal RPA. The RPA products may then be detected with a nanoparticle-based multiplex assay 402, such as a QD barcode assay. An analysis step 403 may be added to analyse the results of the assay.

In order to aid in the understanding and preparation of the present invention, the following illustrative, non-limiting examples are provided.

EXAMPLES

Example 1

Quantum Dot Synthesis

Quantum dots (CdSeS alloyed-ZnS capped) of peak emission wavelength 540 nm ("QD540") were purchased from CytoDiagnostics and used as instructed. Quantum dots of peak emission wavelengths 515 nm ("QD515"), 547 nm ("QD547"), 560 nm ("QD560"), 589 nm ("QD589"), 596 nm ("QD596"), 615 nm ("QD615"), and 640 nm ("QD640") were synthesized and characterized according to published procedures [9, 10] and stored in chloroform at room temperature until later use.

Quantum Dot Barcode Synthesis

Quantum dot barcodes were prepared by mixing together the quantum dots (QD515, QD540, QD547, QD560, QD589, QD596, QD615 and QD640) in different ratios with a polymer-based solution. The polymer solution consisted of poly(styrene-co-maleic anhydride) (32%, cumene terminated) from Sigma-Aldrich dissolved in chloroform, with the polymer concentration at 4-wt %.

The resultant quantum dot polymer solution was then introduced into a nozzle system from 290 Ingeniatrics using a syringe pump from Harvard Apparatus at a rate of 0.9 mL/hour, as well as double distilled (DD) water as the focusing fluid at a rate of 180 mL/hour. The nozzle system was then submerged inside a beaker partially filled with double distilled water. The polymeric barcode microbeads were synthesized in situ, and the microbeads formed a white colloidal suspension in the water. After synthesis, the valve was closed and the microbeads were stabilized by overnight stirring and then collected. The microbeads were filtered using 35 μm BD Falcon nylon mesh strainer cap, and characterized using an automated Beckman Coulter Vi-Cell counter, and stored in DD water at 4° C. until use. The quantum dot concentrations required for preparing the seven different barcodes are presented in Table 1.

TABLE 1

List of microbeads synthesized.

| Barcode | Diameter (μm) | QD540 Concentration (μL/mL) | QD589 Concentration (μL/mL) | QD640 Concentration (μL/mL) |
|---|---|---|---|---|
| B1 | 2.70 ± 1.61 | 60 | | |
| B2 | 2.70 ± 1.36 | | 57 | |
| B3 | 2.70 ± 1.60 | 60 | 11.4 | |
| B4 | 2.70 ± 1.60 | 12 | 57 | |

TABLE 1-continued

List of microbeads synthesized.

| Barcode | Diameter (μm) | QD540 Concentration (μL/mL) | QD589 Concentration (μL/mL) | QD640 Concentration (μL/mL) |
|---|---|---|---|---|
| B5 | 2.70 ± 1.34 | | 57 | 182 |
| B6 | 3.50 ± 1.19 | | | 910 |
| B7 | 2.70 ± 1.51 | | | 182 |

Excitation, Absorption, and Emission Spectra Measurement

The excitation and emission spectra of the Yellow and Nile Blue microbeads were measured using the Excitation and Emission Acquisition modes, respectively, on Horiba Jobin Yvon FluoroMax-3 fluorometer. The quantum dot absorption spectra were measured using Shimadzu UV-1601PC UVVisible spectrophotometer. The quantum dot barcode emission spectra were measured using the Emission Acquisition mode on Horiba Jobin Yvon Fluoro-Max-3 fluorometer.

Sensitivity Assay

Figure 7A:
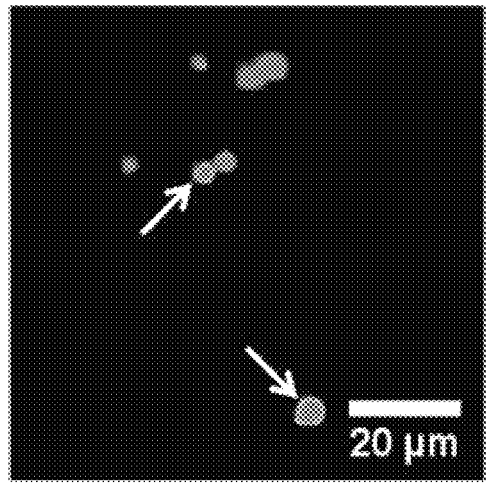
FIGS. 7A to 7D are visual demonstration of a barcode assay and device assay sensitivity.
Figure 7C:
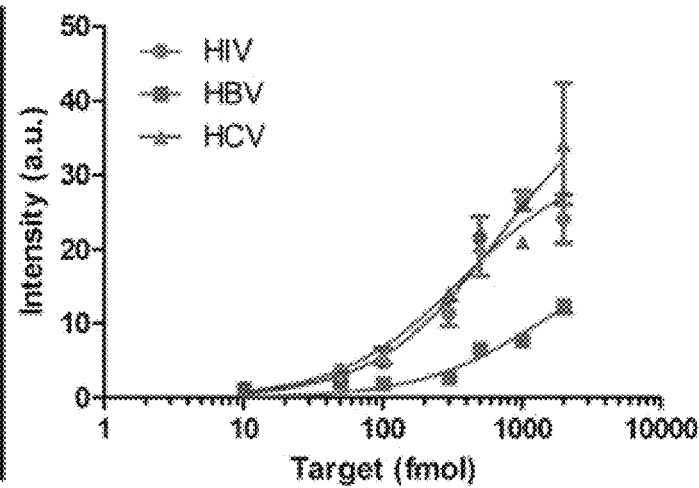
Figure 7B:
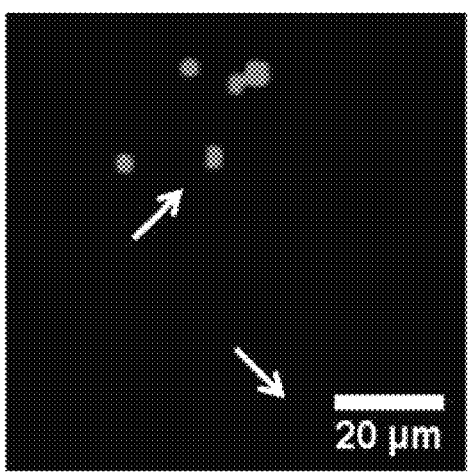
Figure 7D:
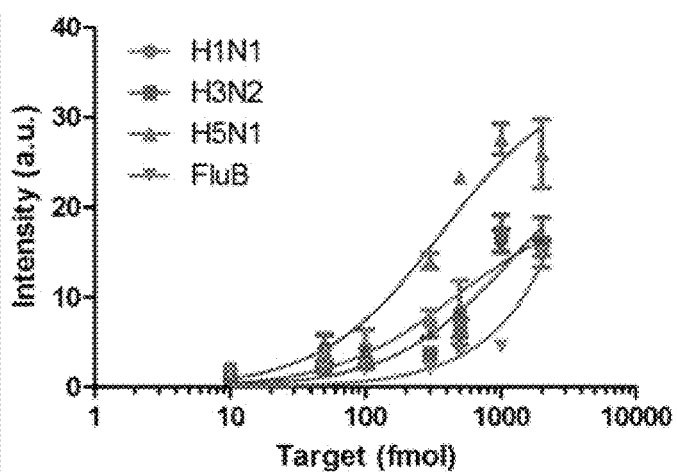

Sensitivity assays (FIGS. 7C and 7D were performed directly on the microwell chips for all infectious disease DNA target strands (T_H1N1, T_H3N2, T_H5N1, T_FluB, T_HIV, T_HBV, and T_HCV) and their respective conjugated barcode beads (B_H1N1, B_H3N2, B_H5N1, B_FluB, B_HIV, B_HBV, and B_HCV). DNA target strands from Bio Basic Inc., purchased HPLC-purified and used without further purification, were prepared in increasing concentrations of 0, 5, 10, 50, 100, 500, 1000, and 2000 fmol/μL in TE buffer. DNA detection strand from IDT DNA Technologies with Alexa647 fluorophore on the 5' end, purchased HPLC-purified and used without further purification, were prepared with concentration of 100 pmol/μL in TE buffer. Both DNA target and detection strand samples were stored at 4° C. until further use. To perform the assay, 1 μL of the conjugated microbead sample, corresponding to approximately 104 conjugated beads, was deposited on a microwell chip for each assay condition and let dry for 1 hour. Then, 1 μL of each DNA target strand sample was mixed with 5 μL of hybridization buffer (10×SSC, 0.1% SDS, heated to 60° C.), 3 μL of DD water, and 1 μL of DNA detection strands or DD water (for the blank condition). This resulted in a total hybridization volume of 10 μL for each assay condition, which include blank, 0, 10, 50, 100, 300, 500, 1000, and 2000 fmol target DNA. The hybridization solution for each assay condition was deposited over the conjugated microbead spots on the microwell chips and incubated at 37° C. for 20 minutes. The microwell chips were then submerged in 10 mL of washing buffer (0.5×SSC, 0.1% SDS, heated to 37° C.), washed by agitation for 20 s, then let dry for 5 minutes before being imaged. Note that care must be taken so that the washing buffer does not dry and crystallize over the sample spots.

Multiplexing Assay

Cross reactivity between the bloodborne virus DNA target strands (T_HIV, T_HBV, and T_HCV) and their corresponding conjugated barcodes (B_HIV, B_HBV, and B_HCV), as well as positive and negative control cases (B_Pos and T_Pos, and B_Neg and T_Neg, respectively), was studied (FIG. 8). First, 6 μL of each conjugated barcode sample, corresponding to approximately 6×10⁴ barcodes each, were mixed together with 90 μL of DD water to produce a 4× dilution factor of the original. The dilution was to reduce microbead aggregation after deposition on chip, which may confound barcode resolution during analysis. To perform the assay, 8 μL of the diluted conjugated barcode mixture, corresponding to approximately 2×10⁴ conjugated beads, was deposited on a microwell chip for each multiplexing case and let dry for 4 hours. Then, 4 μL of each target case (DD water for the negative conditions, and corresponding DNA target strand sample with concentration of 2 pmol/μL for the positive conditions) was mixed with 40 μL of hybridization buffer (10×SSC, 0.1% SDS, heated to 60° C.) and 20 μL of the detection strand (concentration of 100 pmol/μL). This resulted in a total hybridization volume of 80 μL for each multiplexing case. From this, 20 μL of the hybridization solution for each multiplexing case was deposited over the conjugated barcode spots on the microwell chip and incubated at 37° C. for 20 minutes. The microwell chip was then submerged in 10 mL of washing buffer (0.5×SSC, 0.1% SDS, heated to 37° C.), washed by agitation for 20 s, washed again in another 10 mL of washing buffer to further reduce non-specific binding, and then let dry for 5 minutes before being imaged. Note that care must be taken so that the washing buffer does not dry and crystallize over the sample spots.

Whole Blood Collection/Separation, Viral DNA/RNA Extraction, and Reverse Transcription Whole blood was collected by venipuncture in either a Vacutainer (serum) or anticoagulant-treated tubes (plasma). Tubes were inverted several times, and stood upright for 30-60 minutes (for serum collection). Samples were then spun in a refrigerated centrifuge, and serum or plasma was aliquoted and stored at −80° C. HBV or HIV nucleic acid was extracted using the Chemagic Viral DNA/RNA Kit (PerkinElmer), and HIV RNA was then reverse transcribed as per the iScript cDNA Synthesis kit (Bio-Rad).

Recombinase Polymerase Amplification (RPA) and Purification

RPA was performed using either extracted DNA or reverse-transcribed cDNA using the TwistAmp Basic kit (TwistDx, UK). For HBV detection, a premix solution containing 0.48 pmol/μL of each forward and reverse primers (5'-GGCATGGACATTGACCCTTATAAAGAAT-TTGG-3' (SEQ ID NO: 1), 5'-TGTCGAGAAGGTCCCGAATAGACGGAAAGA-3' (SEQ ID NO: 2)), 9.2 μL of nuclease-free water, 29.5 μL of rehydration buffer, and 4 μL of the either extracted healthy or viral DNA was prepared in a volume of 47.5 μL. This solution was then transferred to a tube containing the reaction pellet and mixed. The reaction was initiated by the addition of 2.5 μL of 280 mM magnesium acetate, and incubated at 37° C. for 10 minutes to produce 100 base-pair amplicon.

For HIV detection, a premix solution containing 0.48 pmol/μL of each forward and reverse primers (5'-GAAAGGTGAAGGGGCAGTAGTAATACAAGACA-3' (SEQ ID NO: 3), 5'-CCACACAATCATCACCTGC-CATCTGTTTTCCA-3' (SEQ ID NO: 4)), 11.2 μL of nuclease-free water, 29.5 μL of rehydration buffer, and 2 μL of the either extracted and reverse-transcribed healthy or viral cDNA was prepared for a total volume of 47.5 μL. This solution was then transferred to a tube containing the reaction pellet and mixed. The reaction was initiated by the addition of 2.5 μL of 280 mM magnesium acetate, and incubated at 37° C. for 30 minutes to produce 116 base-pair amplicon.

RPA products were purified using EZ-10 Spin Column DNA Gel Extraction Kit (Bio Basic), and eluted into 50 μL for detection. Purified DNA was visualized by gel electrophoresis, and kept at 4° C. until later use.

Mono-Infection Assays using Amplified Clinical Samples

Clinical mono-infection assays FIGS. 9A to 9D were performed directly on the microwell chips using healthy, HIV-, and HBV-positive samples after amplification. DNA detection strands from IDT DNA Technologies with Alexa647 fluorophore on either 5' end (CD_HIV) or 3' end (CD_HBV), purchased HPLC-purified and used without further purification, for the HIV and HBV target sequences, were prepared with concentration of 100 pmol/μL in TE buffer and stored at 4° C. until further use. To perform the assay, 1 μL of the conjugated microbead sample, corresponding to approximately 104 conjugated beads, was deposited on a microwell chip for each assay condition and let dry for 1 hour. During this time 20 μL of the sample was mixed with 5 μL of the corresponding detection strand and denatured at 100° C. for 15 minutes. Then, the 25-μL denaturation solution was mixed with 25 μL of hybridization buffer (10×SSC, 0.1% SDS, heated to 60° C.). The 50-μL hybridization solution was deposited over the dried conjugated microbead spot on the microwell chip and incubated at 37° C. for 60 minutes, and let cool at room temperature for 5 minutes. The microwell chip was then submerged in 200 mL of washing buffer (0.5×SSC, 0.1% SDS, heated to 37° C.), washed by agitation for 10 s, washed again in another 200 mL of washing buffer to further reduce non-specific binding, and let dry for 5 minutes before being imaged. Note that care must be taken so that the washing buffer does not dry and crystallize over the sample spots.

Co-Infection Assays Using Amplified Clinical Samples

Cross-reactivity between the amplified HIV and HBV clinical samples (CT_HIV and CT_HBV) and their corresponding conjugated barcodes (CB_HIV and CB_HBV), as well as positive and negative control cases (CB_Pos and CT_Pos, and CB_Neg and CT_Neg, respectively), was studied (FIGS. 9E to 9H). First, 5 μL of each conjugated barcode sample, corresponding to approximately 5×104 barcodes each, were mixed together with 20 μL of DD water to produce a 2× dilution factor of the original. The dilution was to reduce microbead aggregation after deposition on chip, which may confound barcode resolution during analysis. To perform the assay, 1 μL of the diluted conjugated barcode mixture, corresponding to approximately 5×10³ conjugated beads, was deposited on a microwell chip for each multiplexing case and let dry for 1 hour. During this time 10 μL of each sample was mixed with 5 μL of each of the corresponding detection strands (5 μL of CD_HIV, 5 μL CD_HBV, and 10 μL of 405 CD for both CT_Pos and CT_Neg) and denatured at 100° C. for 15 minutes. Then, the 60 μL denaturation solution was mixed with 60 μL of hybridization buffer (10×SSC, 0.1% SDS, heated to 60° C.). The 120 μL hybridization solution was deposited over the dried conjugated microbead spot on the microwell chip and incubated at 37° C. for 60 minutes, and let cool at room temperature for 5 minutes. The microwell chip was then submerged in 400 mL of washing buffer (0.5×SSC, 0.1% SDS, heated to 37° C.), washed by agitation for 10 s, washed again in another 400 mL of washing buffer to further reduce non-specific binding, and let dry for 5 minutes before being imaged. Note that care must be taken so that the washing buffer does not dry and crystallize over the sample spots.

Device Design and Construction

The device was designed using SolidWorks 2012 and 3D printed commercially (Reprodux, North York, Ontario, Canada). Laser diode excitation sources of 405 nm 50 mW (http://www.ebay.com/itm/170719374707), and 650 nm 50 mW (http://www.ebay.com/itm/1pcs-650 nm-50 mw-Red-Laser-Diode-Dot-Module-/370650098149?pt=LH_DefaultDomain_0&hash=item564c77a9e5) were purchased online and secured into the device as delivered. The device was designed such that both lasers could excite the same spot on the chip. An excitation filter $\lambda_{ex}$=655/15 nm (Edmund Optics) was fixed in front of the 650 nm laser diode source to reduce background signal. Both laser diodes were electrically connected to 2× AA batteries via a battery holder and single-pole triple-throw switch (both purchased from a local electronics shop) that switches between the two sources as well as an OFF state. A generic 160×-200× pocket microscope was purchased online (http://www.gadgetplus.ca/science/Microscope160-200×.html). It was disassembled to extract the eyepiece and objective lenses, and installed into the device manually. The eyepiece was fixed in place but the objective was made to be movable long a track to allow focusing on the sample.

Sample Imaging

All images were acquired using the iPhone® 4S from Apple® (unless otherwise specified), mounted in the device of the present invention. Quantum dot barcodes and Alexa647 fluorophore were excited using laser diodes of wavelengths 405 nm and 650 nm, respectively. Emission filters $\lambda_{em}$=430 LP (Thorlabs), $\lambda_{em}$=530/10 (Thorlabs), $\lambda_{em}$=580/10 (Thorlabs), $\lambda_{em}$=640/10 (Thorlabs), and $\lambda_{em}$=692/40 (Semrock, Brightline Cy5-4040A) were placed in the device's emission filter slot one at a time during imaging. The emission filter $\lambda_{em}$=430 LP was used in conjunction with a neutral density filter OD=1.3 (Thorlabs) to image all barcodes to determine their size and location, while avoiding intensity saturation. The emission filters $\lambda_{em}$=530/10, $\lambda_{em}$=580/10, and $\lambda_{em}$=640/10 corresponded with quantum dots QD540, QD589, and QD640, respectively, and were used to isolate for their fluorescence for resolving barcodes. The emission filter $\lambda_{em}$=692/40 was used to isolate for the detection strand Alexa647 secondary label fluorescence as a means to measure the amount of analyte that hybridized with its corresponding capture strand. Image exposure times, made adjustable with the use of the NightCap app from Apple's App Store, was maintained at 1 s for all filters. In the case of fluorophore particles, they were excited using only the 405 nm laser diode source and imaged using only the emission filter $\lambda_{em}$=430 LP, the images of which were used for subsequence intensity analysis Image Analysis A custom-made algorithm was written in MathWork's MATLAB for all image analysis. The algorithm accepts as inputs five emission filter images ($\lambda_{em}$=430 LP, $\lambda_{em}$=530/10, $\lambda_{em}$=580/10, $\lambda_{em}$=640/10, and $\lambda_{em}$=692/40) that include samples and the same filter images of the microwell chips without beads for background intensity adjustment. The images were cropped to include beads of interest based on user selection. The cropped filter images were aligned with the $\lambda_{em}$=430 LP filter image through the use of the Discrete Fourier Transform registration (17, 18). The algorithm then identified the size and location of each bead, based on its appearances in the $\lambda_{em}$=430 LP filter image, using the Hough transform (19, 20). Each bead was then associated with the mean pixel intensity across its area at each of the four remaining filter images. For each bead, the $\lambda_{em}$=530/10, $\lambda_{em}$=580/10, and $\lambda_{em}$=640/10 filter image intensities comprised its intensity profile, while the $\lambda_{em}$=692/40 filter image intensity indicated the secondary probe intensity. In order to identify the barcodes on the chip, known barcode intensity profiles were first established. These profiles were obtained by imaging all the barcodes—B_H1N1, B_H3N2, B_H5N1, B_FluB, B_HIV, B_HBV, B_HCV, B_Pos, B_Neg, CB_HIV, CB_HBV, CB_Pos, and CB_Neg—alone (FIG. 7) and calculating the median filter intensity across all beads for each filter. A microbead's intensity profile was then compared against each known barcode's intensity profile to identify the barcode of interest. Specifically, a barcode was classified according to its type (i.e. synthetic or clinical sample) and highest to lowest intensities among the filters $\lambda_{em}$=530/10, $\lambda_{em}$=580/10, and $\lambda_{em}$=640/10. This narrowed the selection down to either one barcode, in which case the barcode of interest was identified, or two barcodes. Between the two possibilities $B_{high}$ (with higher mean intensities) and $B_{low}$ (with lower mean intensities) a threshold was defined for $B_{low}$:

$$I_{barcode}=I_{mean}+I_{STD} \quad [1]$$

$I_{barcode}$=Intensity threshold for $B_{low}$.

$I_{mean}$=Mean intensity of $B_{low}$.

$I_{STD}$=Intensity standard deviation of $B_{low}$.

This threshold was calculated for the highest intensity amongst the three filters $\lambda_{em}$=530/10, $\lambda_{em}$=580/10, and $\lambda_{em}$=640/10 for $B_{low}$. If the highest intensities were similar in value between $B_{low}$ and $B_{high}$, the second highest filter intensity was used. With this, if the microbead's corresponding filter intensity was equal to or lower than $I_{barcode}$, the barcode of interest was $B_{low}$, otherwise $B_{high}$ was chosen.

A microbead B is imaged during a synthetic sample multiplexing test 480—thus classified as 'synthetic sample'—has an intensity profile of [$\lambda_{em}$=530/10, $\lambda_{em}$=580/10, $\lambda_{em}$=640/10]=[4, 40, 80], so [$\lambda_{em}$=640/10]>[$\lambda_{em}$=580/10]>[$\lambda_{em}$=530/10]. On examination the set of barcodes used for synthetic multiplexing, B has a similar intensity profile (i.e. same order of highest to lowest filter intensities) as B_Pos and B_Neg. Between them, B_Neg has the lower mean intensities and thus chosen as $B_{low}$, with the its highest filter intensity at [$\lambda_{em}$=640/10]=30.50. And because it is much lower and thus distinguishable from B_Pos's [$\lambda_{em}$=640/10]=80.35, the intensity threshold is calculated using B_Neg's [$\lambda_{em}$=640/10]:

$$I_{barcode}=I_{mean}+I_{STD}=30.50+6.26=36.76.$$

Since B's [$\lambda_{em}$=640/10]=80 is greater than $I_{barcode}$=36.76 from B_Neg, B is identified as B_Pos.

We determined whether the analyte of interest is present by using the intensity values from the $\lambda_{em}$=692/40 filter, which isolates for the Alexa Fluor 647 secondary probe signal. For the synthetic sample sensitivity assays the intensities were used directly to establish the limit of detection and dynamic range for the device. However, we used a bead-counting method to determine the optical detection of multiplex samples and clinical samples because we achieve greater accuracy in the measurement when the measurement is based on a comparison to negative controls. Negative and positive controls are always required in analyzing complex samples, as these control samples confirm whether a technique is working as designed. When we conduct the measurements, we develop a histogram of the fluorescence intensity from the secondary probe and compare that signal to those of the negative sample. Equation 2 describes this analysis.

$$Q=\text{(population of barcode whose } \lambda_{em}\text{=692/40 filter intensity} \geq I_{assay}\text{)/(total barcode population)} \quad [2]$$

That is, the barcodes whose secondary probe intensities were equal to or above the threshold $I_{assay}$, defined empirically, were counted and a percentage, relative to the barcode's total population, was calculated. In the case of multiplexed detection of synthetic bloodborne viral targets (FIG. 8), a detection was considered positive if Q>30% (i.e. over 30% of said barcode had secondary probe signals above the threshold). In the case of amplified mono- and co-infected clinical samples (FIG. 9), a detection was instead considered positive if Q>3% due to their overall lower signals.

Statistics and General Methods

All data represent analysis from at least 100 barcodes to ensure they are representative of the experimental conditions studied. The variability in the number of barcodes analyzed is due to the field of view. In some cases, there are more beads per field of view than others. Once we analyze >100 barcodes, the measurements were relatively consistent and did not influence the statistics. For the detection of mono-infected patient samples, we used healthy subject samples as a negative control, which is procedurally and clinically more accurate as negative controls than any other types of samples. To ensure clinical sample blindness, they were prepared and provided unlabeled by the collaborators to the investigators, who then performed the experiments without knowledge of the samples' identities. For where statistical tests were necessary (i.e. comparing the healthy subjects group with the HIV- or HBV-infected subject groups), the two-sided t-test was used because the data exhibits normal distribution.

Human Subjects

The de-identified clinical samples were obtained from the Toronto Western Hospital Liver Clinic and St. Michael's Hospital biobank repository. The protocol was approved by the Research Ethics Board of the University Health Network and St. Michael's Hospital, both affiliates of the University of Toronto. All patients provided written informed consent for storage and use of their specimens for research.

Results

Quantum Dot Barcode Synthesis and Characterization

ZnS-capped CdSeS quantum dot barcodes were incorporated into polystyrene microbeads using a flow-focusing strategy, as described in a previous publication [4]. Briefly, different emitting quantum dots were mixed in chloroform with the poly(styrene-co-maleic anhydride). When this chloroform solution intersects with a high pressure water stream inside a nozzle, microfluidic instability causes the fluid to pinch off and form beads. The optical properties of these quantum dot beads reflect the combination and concentration of the quantum dots in the chloroform solution. Flow cytometry is used to confirm that the barcodes contain distinctive optical emission from each other, so that each barcode can identify the genetic target of interest. The maleic anhydride converts into a carboxylic acid functional group, which allows the barcoded beads to conjugate to a targeting molecule using carbodiimide chemistry.

Integration of Quantum Dot Barcoding With Smartphone Technology

A multiplex-chip platform that is simple to use and can be easily transported were two of the main design foci of the point-of-care device of the present invention. To this end, the inventors arrayed quantum dot barcodes on microfabricated slides with controlled number of microbeads per unit area. Barcodes in a chip format are easier to transport than when they are in solution. Microbead arrays on a chip are currently used in sequencing analysis but the cost of the final chip is high because the microbeads are arrayed on the ends of optical fibers [5]. Current arraying techniques of fluorescence microbeads are not cost-effective for conventional diagnostic applications for point-of-care use in either resource-rich or resource-limited settings. We developed a simple method to array quantum dot barcodes on the surface of a chip. Glass slides were microfabricated with 3.0 μm-diameter wells. A solution of ~3.0 μm sized microbead barcodes containing different combinations of fluorescence emitting CdSeS alloyed-ZnS quantum dots were added to the chip. They spontaneously settled into each well, reducing overlapping and aggregation that may confound analysis of their fluorescence in later steps. Once bound, these microbeads do not desorb from the surface as they are held in place by non-covalent forces. The concentration and size of the barcodes determine the filling efficiency. The deposition of barcodes on the chip, compared to those stored in solution, enables higher portability of barcodes and reduces the number of steps in the quantum dot barcode assay process.

The device itself is also portable and easy to use (FIG. 5B). The components—batteries, switch, laser diodes, lenses, and filters—and 3D-printed plastic chassis are all lightweight and able to fit in one hand. The two laser diodes are switched on independently via a manual switch: Excitation Laser 1 (405 nm) excites the barcodes and Excitation Laser 2 (650 nm) excites the secondary label with a filter ($\lambda$ex=655/15) that controls the wavelength excitation observed by the chip. The eyepiece and movable objective lens magnifies and focuses barcodes on the chip to allow them to be viewable clearly by the naked eye on the smartphone display. The smartphone camera, in this case Apple's® iPhone 4S®, then captures that view. A total of five images are acquired for each sample, corresponding to each of the five emission filters ($\lambda$em=430LP, 530/10, 580/10, 640/10, and 692/40). Specifically, the 430LP filter image is used for extracting the location and size of the barcodes in the camera field-of-view; the 530/10, 580/10, and 640/10 filter images for isolating quantum dot signals to determine barcode signatures; and the 692/40 filter image for isolating the secondary label signal to determine the presence of target analyte bound to the barcode surface. Finally, a custom-written algorithm analyzes these images and produces the results. The algorithm develops a histogram of the optical signal from the secondary probe of all barcodes within the sample. A threshold is established in a measurement based on the highest signal from barcodes that do not contain any of the target molecules of interest (i.e. the negative control in the experiments). A graph of barcode numbers above this threshold is used to determine a positive or negative detection. We expect samples that have the target molecule of interest to have more barcodes above this threshold. We chose this method of analysis rather than using absolute intensity values because we found this method to obtain greater consistency in the analysis due to reduction in skewing of the measurements from a small population of beads. Our measurement strategy is adapted from flow cytometry, where the quantification is based on single cell count instead of a population average. The entire imaging and analytical process takes about ten minutes and can be performed with minimal training.

Use of Quantum Dots Over Traditional Fluorophores

The unique optical properties of the quantum dots for barcoding are important for engineering a low-cost multiplex point-of-care device. Here we compared the optical properties of two microbeads encapsulated with organic fluorophores ('Yellow' with $\lambda_{em}$=480 nm, and 'Nile Blue' with $\lambda_{em}$=630 nm) versus quantum dots ('QD540' with $\lambda_{em}$=530 nm and 'QD640' with $\lambda_{em}$=640 nm).

Figure 6A:
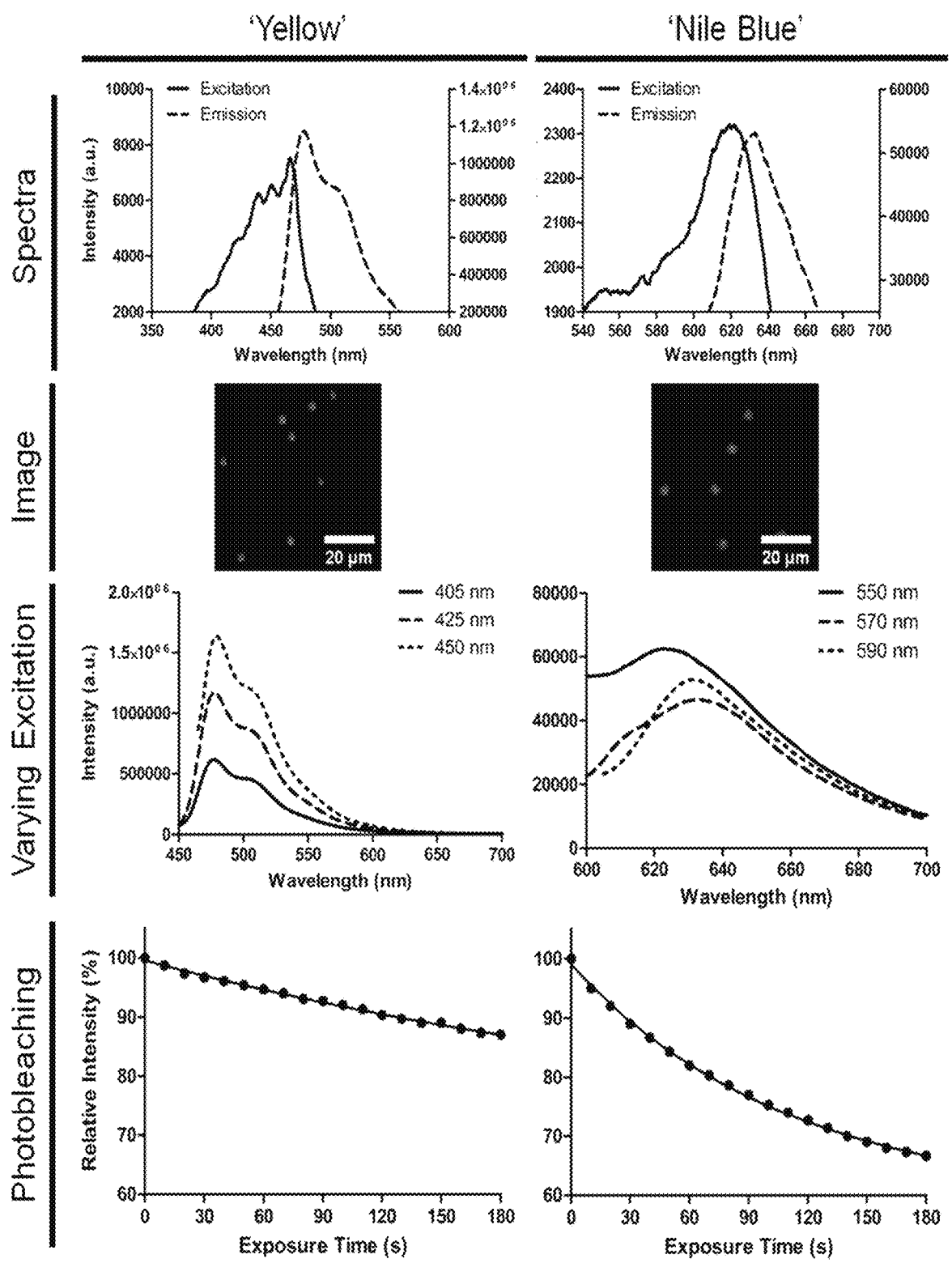
FIGS. 6A to 6B show comparison of the optical properties between organic dye molecules and quantum dot inside polystyrene beads. Polymeric particles impregnated with fluorophores ('Yellow' and 'Nile Blue'.
Figure 6B:
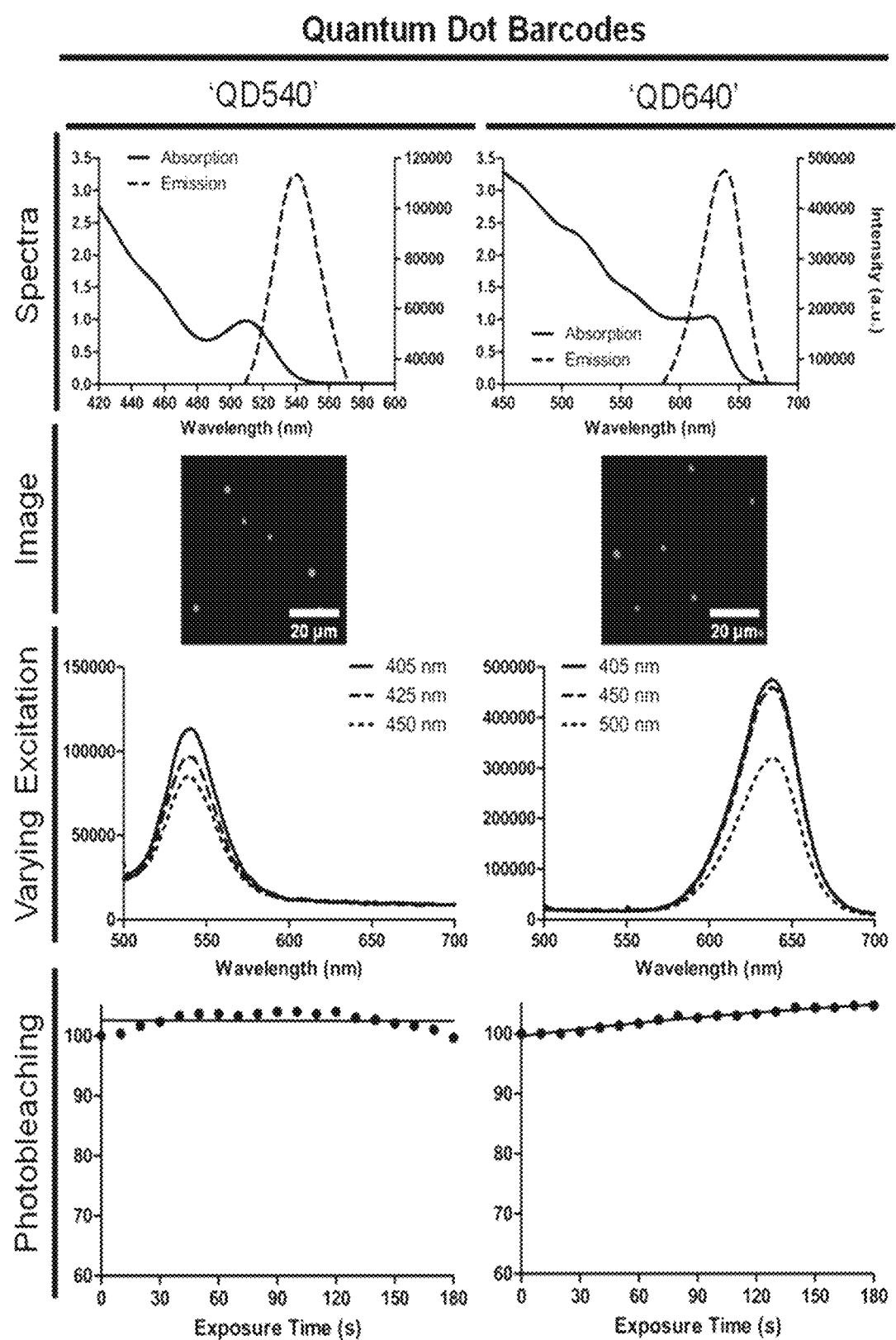

Spectra—As shown in FIG. 6, the quantum dots have a continuous absorption profile (FIG. 6A 'Spectra') while the organic fluorophore has a peak-like profile (FIG. 6B 'Spectra'). The absorbance profile presents a significant advantage for quantum dots for engineering point-of-care device. This would reduce the size of the final device and reduce costs as a quantum dot-barcode device will only require a single energy source to excite all of the barcodes (in this case, we used a 405 nm diode laser) while the organic fluorophore-barcodes will require multiple emitting diodes or lasers to maximally excite different barcodes.

Varying Excitation—The quantum dot barcodes also have narrower emission profiles (e.g. full-width half-max of ~35 nm versus 60 nm for 'QD540' (FIG. 6B) and 'Yellow' (FIG. 6A), respectively) and retain their emission peaks despite being excited by different wavelengths (e.g. 'QD640' (FIG. 6B) versus 'Nile Blue' (FIG. 6A)) (FIG. 6 'Varying Excitation'). These properties allow false barcode identification to be reduced and would enable greater number of barcodes to be engineered for multiplexing analysis.

Photobleaching—Finally, the quantum dot barcodes are much more resistant to photobleaching (FIG. 6B) compared to the organic fluorophore (FIG. 6A) encapsulated barcodes (FIG. 6 'Photobleaching'). This is important for accurate barcode identification as bleaching of the coded microbeads can lead to mis-detection. Using quantum dots for barcoding simplifies the read-out device and reduces the costs of the final device so that it could be broadly used in both resource-rich and resource-limited settings.

Synthetic Targets to Assess Device Sensitivity and Multiplexing Capability

The current detection platforms for identifying quantum dot barcodes require expensive instruments and detectors, which prohibit their use for point-of-care detection [1, 2]. Here we evaluated whether our device can differentiate the optical signals between barcodes as well as the secondary fluorescent probe used in our genetic assays. FIGS. 7A and 7B demonstrate that an iPhone camera is able to capture the distinct optical emissions of each barcode on the microwell chip and proper filtering can differentiate the barcode optical signal from the secondary probe's signal. These studies confirmed that an iPhone® camera can image barcodes on the chip surface and be used as a detector for biological assays.

Applicants first determine the analytical performance of the microbead-based sandwich assay using our engineered smartphone reader. We designed seven barcodes for detecting seven infectious disease biomarker targets as shown in FIG. 10 plus two barcodes for the positive and negative control samples. When the target is absent (i.e. negative detection), the optical signal from the microbead comprises only the quantum dot signal of the barcode. When the target is present (i.e. positive detection), the microbead optical signal consists of emissions from both the quantum dots and Alexa Fluor 647 dye secondary probe. The limit of detection and linear dynamic range for each of the targets for HIV, HBV and HCV, and the influenza targets H1N1, H3N2, H5N1, and Flu B (FIGS. 7C and 7D) is between 10 to 50 fmol ($6 \times 10^9$ to $3 \times 10^{10}$ copies) and up to 40-fold, respectively, in a sample volume of 10 μL. This suggests that analytical performance is independent of the infectious disease targets. In comparison to the current gold standard point-of-care diagnostics (i.e., lateral flow immunoassay) used in resource-limited countries, the limit of detection of our device is 104 times lower and has the added feature of detecting multiple targets simultaneously.

Applicants next examined the ability of quantum dot barcodes for multiplex detection. A key advantage of quantum dot barcodes is that the different colors and intensity combinations of quantum dots inside the microbeads can produce a large library of barcodes, providing significant multiplexing capabilities. Nie and co-workers estimated that 10,000 to 40,000 different barcodes could be generated using five to six different emitting quantum dots [3]. For our device, the algorithm is designed to identify the barcodes by comparing the optical signal of each microbead to that of a known panel of barcodes. Here we demonstrated its ability to simultaneously detect multiple synthetic genetic targets from bloodborne virus panel (FIG. 8). We prepared six different mock genetic samples by mixing various combinations of the genetic target sequences for each of the three pathogens of interest—HIV, HBV, and HCV—plus a positive control sequence to ensure that the barcodes are working as designed, and the secondary fluorescent probe sequence. For example, we would prepare solutions that were spiked with the target sequences for HIV and positive control sequence in one combination FIG. 8B, then HIV, HBV, HCV and positive control sequence in another combination (FIG. 8F). A sample of 20 µL was added to the chip and incubated at 37° C. for 20 minutes, rinsed with a washing buffer, dried, imaged, and analyzed using the algorithm. In all cases the target sequences were correctly identified by the assay. For example, in our solution containing the sequences for HCV and positive control (FIG. 4D), the bar graph shows our technique can discriminate between barcodes bound with secondary probes (i.e. HCV and positive control) versus those not bound (i.e. HIV, HBV and negative control). All of the probe recognition sequences for the bloodborne viral panels were carefully designed in silico to minimize cross-reactivity with closely related viruses using subtypes against the gag gene of HIV, core protein gene of HBV and nucleocapsid protein gene of HCV, as per gold standard testing standards.

Clinical Validation of Diagnostic Device

Applicants determined whether the device was capable of detecting and differentiating samples from patients with HIV and HBV from those without (i.e., healthy subjects). The experiment done using synthetic targets showed that the device has a limit of detection of $10^{-15}$ mol but to use the device for diagnosing patient samples, the limit of detection needed to be lowered by a factor of $10^6$. Conventional PCR amplification methods require bulky and expensive equipment that cannot be incorporated into a point-of-care device. To address this issue, we optimized an isothermal amplification step, which can be performed in 10-30 minutes, is simple, and does not require precise temperature control (operates at 37° C.-42° C.).

Figure 9E:
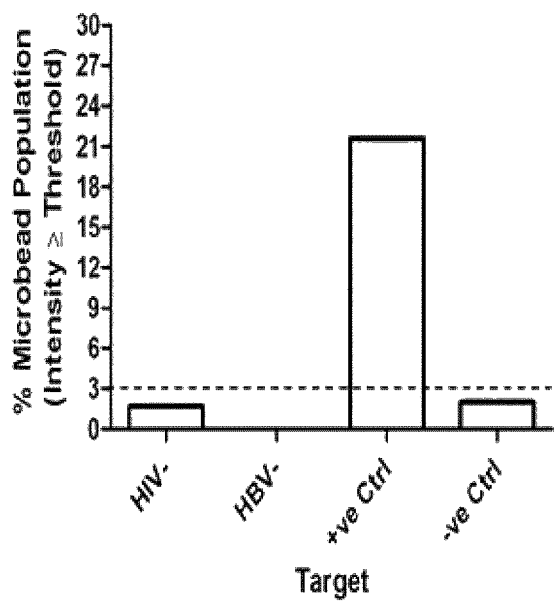
Figure 9F:
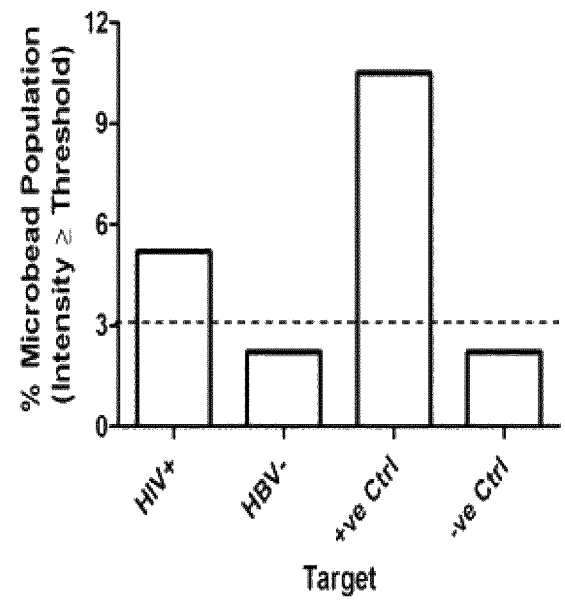
Figure 9G:
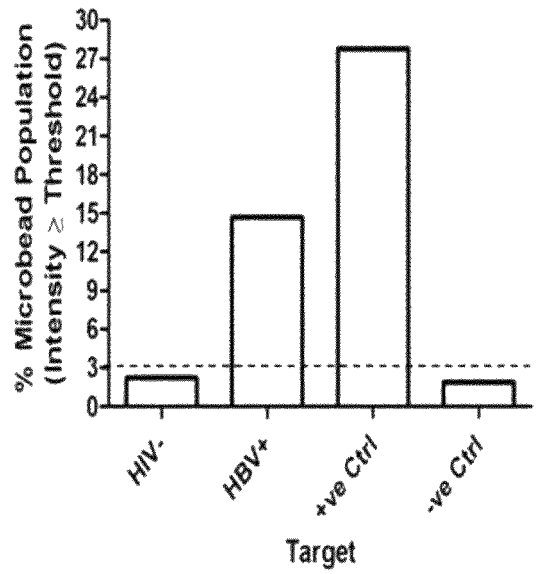
Figure 9H:
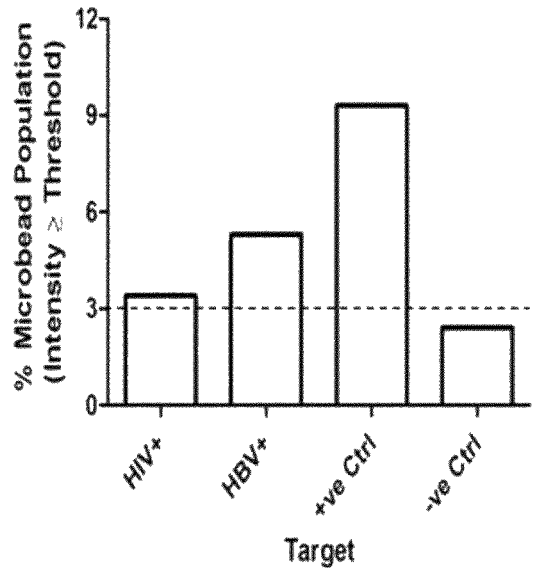
Figure 11B:
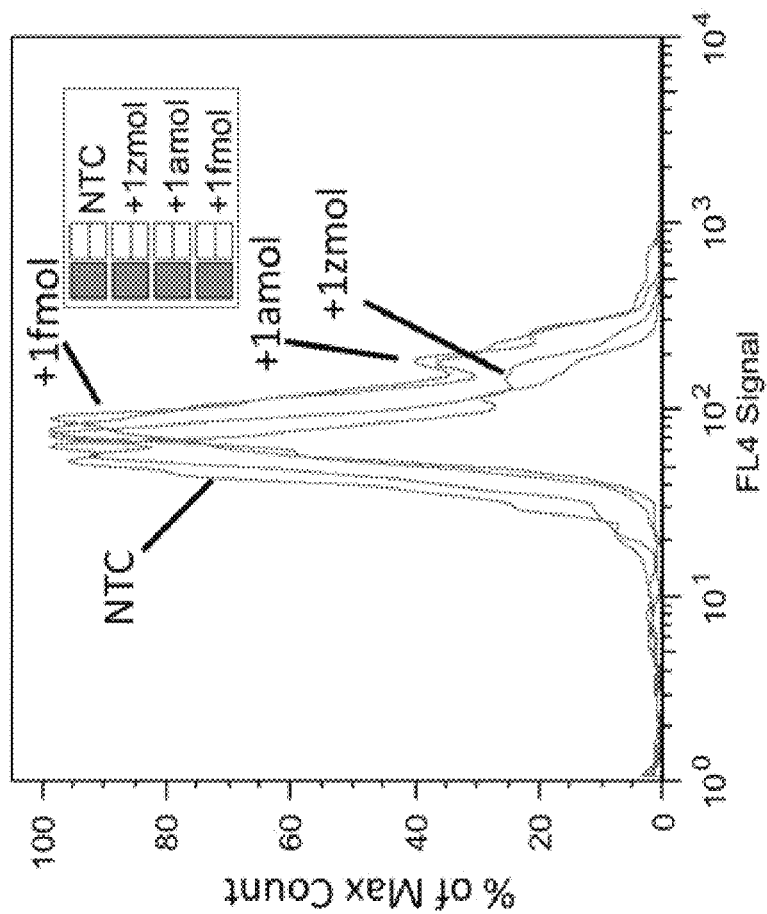
FIG. 11B QD barcode assay was conducted with amplicons produced in panel A, and detection probe signals (FL4) were measured by running flow cytometry.
Figure 11A:
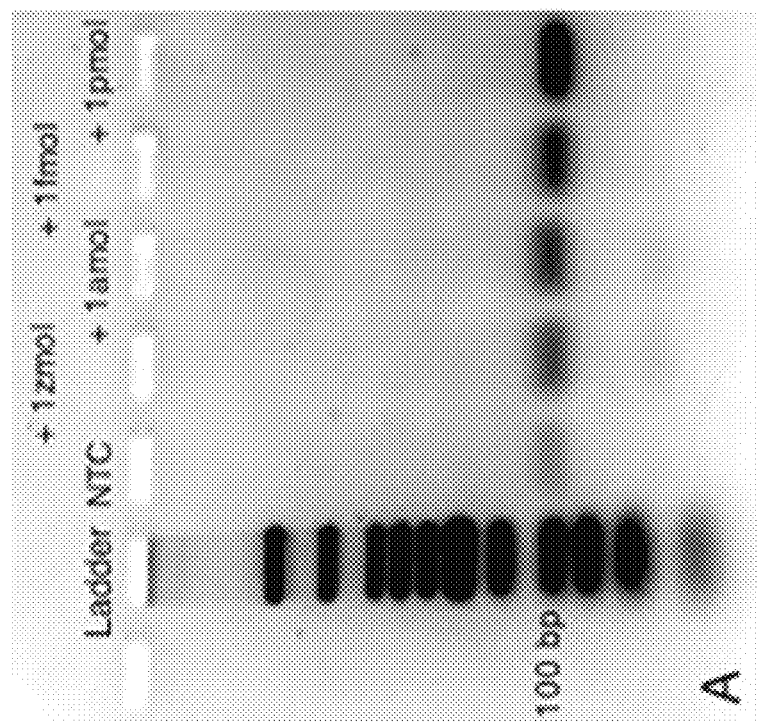
FIG. 11A RPA products visualized on 3% agarose gel electrophoresis (135V, 30 minutes). Various amount of N. Gonorrhoeae template DNA was amplified to produce 100 bp amplicons.
Figures 12A, 12B:
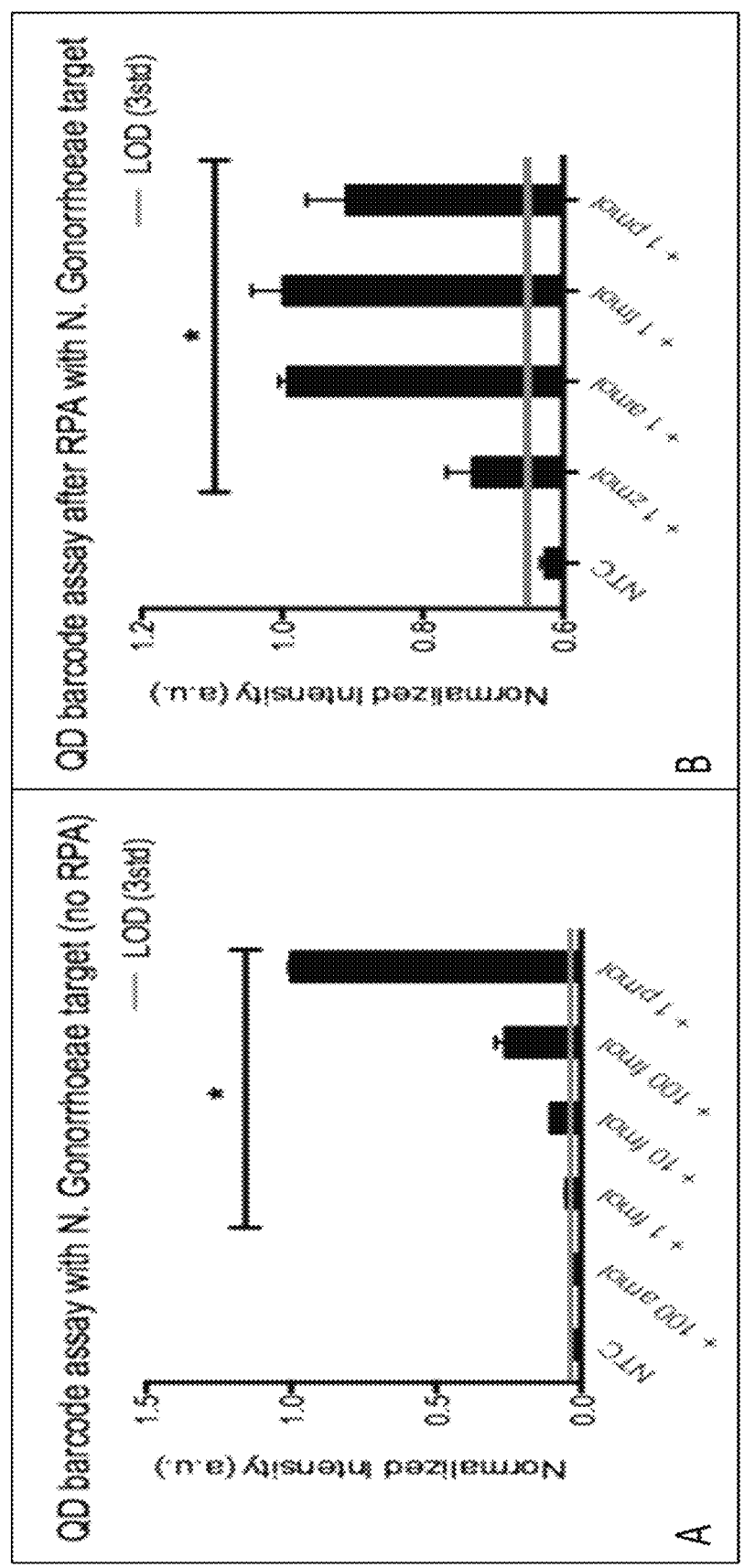
FIG. 12 QD barcode assay conducted with various amount of FIG. 12A unamplified N. Gonorrhoeae template DNA (LOD~1fmol), and FIG. 12B amplified N. Gonorrhoeae template DNA (LOD~1zmol). *Statistical significance was compared with NTC sample by performing two tailed Student'st_test.
Figures 13A, 13B:
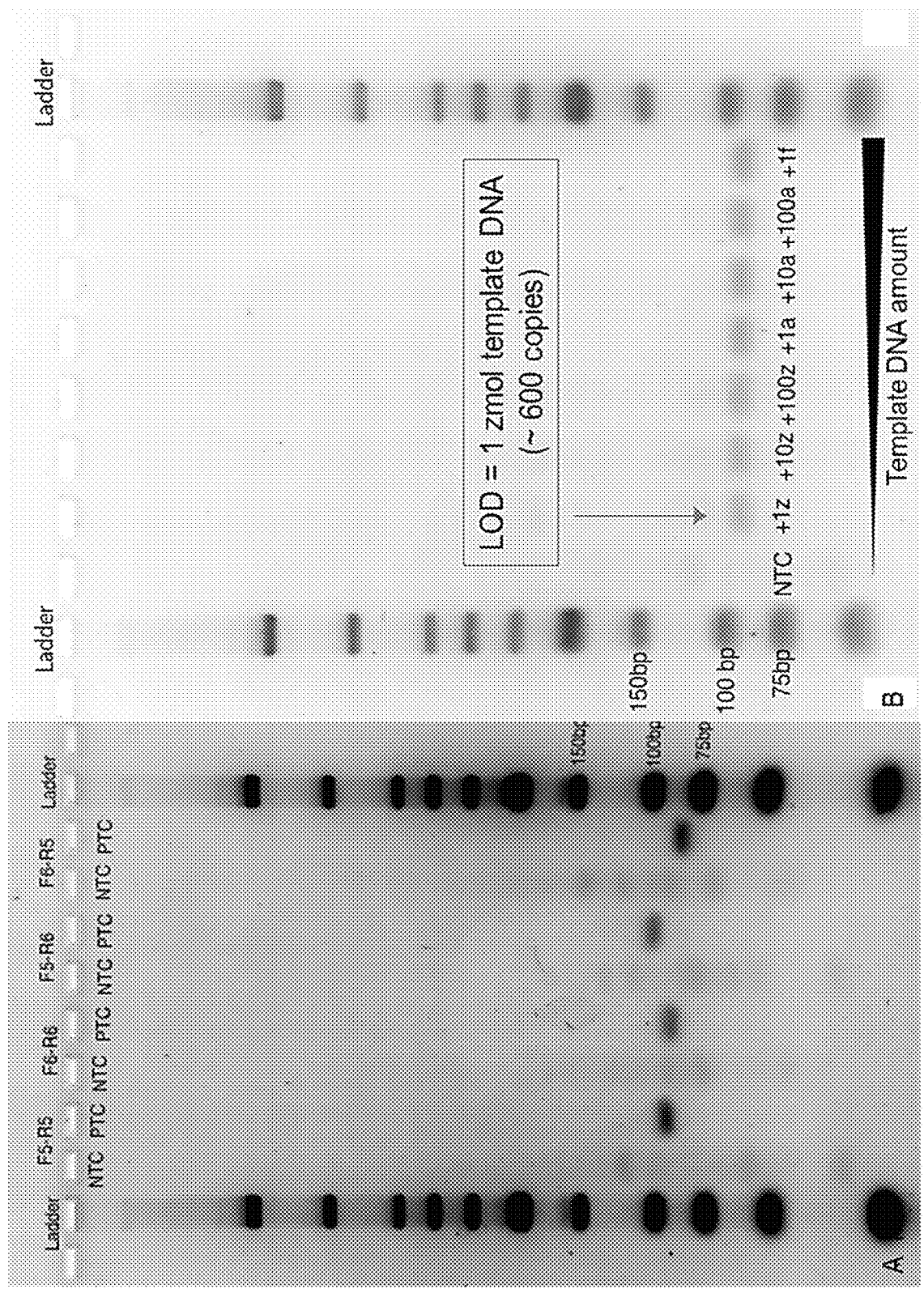
FIG. 13A Four primer pairs (F5-R5, F6-R6, F5-R6, and F6-R5) were screened to optimize RPA reaction. For positive template control samples (PTC), 1amol HPV-16 template DNA was added. F5-R5 primer pair produced the brightest band, and used throughout subsequent experiments.
FIG. 13B Various amount of HPV-16 template DNA were amplified using F5-R5 primer pair.
Figures 14A, 14B:
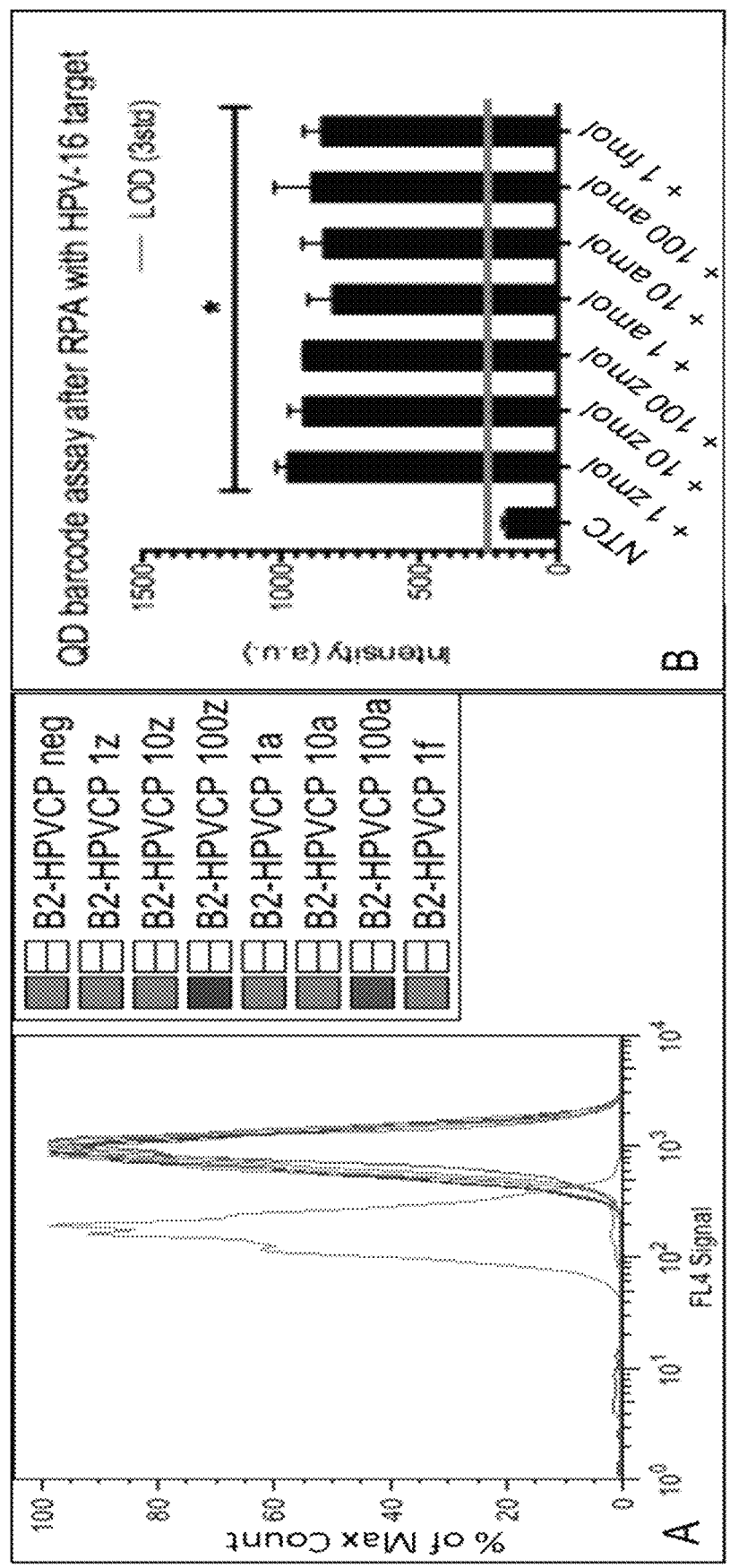
FIG. 14B Average of duplicates plotted with standard deviations (LOD~1 zmol). *Statistical difference was compared with NTC sample by performing two_tailed Student's t_test.
Figure 15:
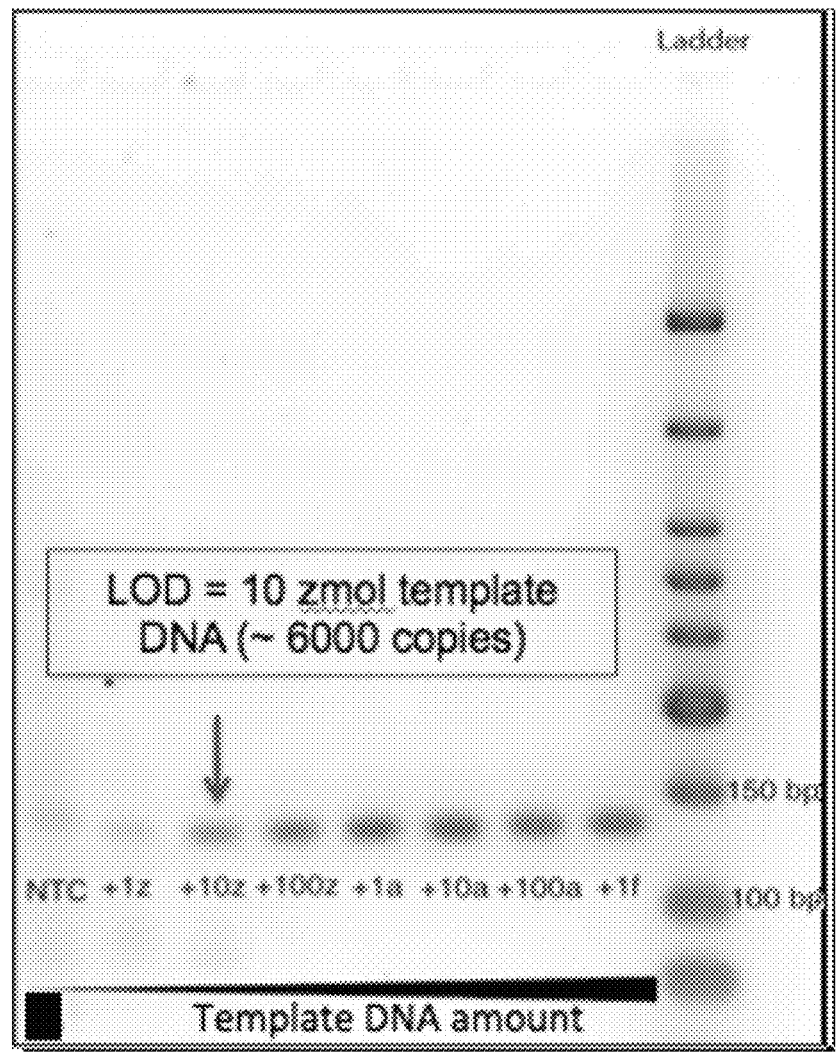
FIG. 15 RPA products visualized on 3% agarose gel electrophoresis (135V, 30 minutes) for various amount of HIV template DNA.

Patient samples were collected using standard protocols and we extracted the hepatitis B viral DNA and HIV viral RNA using magnetic microbeads. The cell membrane was first disrupted by the addition of lysis buffer, and the surface functionalized magnetic microbeads captured viral nucleic acid. The sample was then placed in a magnetic separator to collect magnetic microbeads. Before use in our assay, the HIV RNA was reverse-transcribed into cDNA. All samples were then amplified using recombinase polymerase amplification. The recombinase proteins were added to the isolated genetic targets to form nucleoprotein complex, which facilitates strand-transfer at the homologous sequence of the template DNA. Single-stranded binding proteins then stabilize the displaced strand of the template DNA, and the DNA polymerase extends the complimentary strand [6]. The double-stranded DNA was then denatured and added to the chip, incubated at 37° C., rinsed with a washing buffer, dried, imaged, and analyzed using the algorithm in a manner that is similar to detection of the synthetic targets. FIGS. 9A and 9B demonstrate the successful diagnosis of individual patient samples with HIV and HBV, respectively, of varying viral loads before amplification. The HBV—infected samples were comprised of multiple genotypes to ensure our test would be widely applicable. In order to determine whether the measurement results were significant, we combined the measurements from all samples of healthy subjects and from the infected patients with either HIV or HBV (FIGS. 9C and 9D, respectively). Our results showed a significant difference with a p-value of 0.05 and 0.01 respectively. We further confirmed the results using flow cytometry and showed comparable outcomes. Our diagnostic device is capable of detecting viral loads in the range of $10^3$ to $10^9$ copies per mL and different genotypes. To confirm our device is capable of multiplex detection of patient samples, we mixed amplified patient samples containing HIV and/or HBV. We performed fourplex assays (HIV, HBV, a positive and negative control bead), and the results of which clearly demonstrated that the device is capable of differentiating between two viruses FIGS. 9E to 9H for smartphone device. We further investigated the level of specificity with our genetic assay by sequencing 7 HBV and 10 HIV patient samples. We found that there are 5-9 and 3-4 mismatches within HBV and HIV probe-binding regions used for the assay, respectively. Although only wild-type probes have been used to detect patient samples in this study, the level of specificity can be further extended to detect single base pair mismatch by following Liong, M. et al's approach of using mutant probes that are designed specifically to match mutated region and therefore bind stronger with mutated target than the wild-type target [7]. The development of our point-of-care device for diagnosing single nucleotide polymorphisms was not a focus but such studies will be a focus in future studies. Our clinical validation with real-world HBV- and HIV-infected patient samples demonstrates the effectiveness of the proposed detection platform for diagnosing infectious diseases in point-of-care settings.

All of the pathogen targets used as test panels in this study represent major infectious threats to the global community, necessitating the development of effective and innovative means for detection and informatics to identify infected individuals and accelerate clinical management. HIV, HBV and HCV are prevalent in resource-limited settings and pose major threats to populations, often related to unknown transmission through sexual contact, drug use and contaminated blood products [7, 8]. For more rapidly spreading pathogens, immediate implementation of infection control measures and enhanced surveillance to curb the spread of disease will be critical. Here we have shown that the integration of quantum dot barcodes with smartphone technology can be used for multiplex molecular diagnosis of these infectious diseases with wireless transmission. The steps in the assay are (1) extraction of the genetic target, (2) amplification of the target, (3) recognition and hybridization to barcodes on chip and secondary probe, and (4) read-out of the chip optical signal with the smartphone.

Example 2

Conventional diagnostic methods for infectious diseases are either unaffordable or unavailable in many developing countries (PCR or ELISA tests), or provide only qualitative data with low analytical sensitivity (LFA). Also, these methods have limited capability to diagnose multiple infectious agents simultaneously requiring high operational cost and time. Furthermore, current DNA extraction techniques rely on centrifugation (phenolchloroform separation or silica membrane-based spin column) and manual separation steps using magnetic beads. Consequently, there is an increasing demand for cost-effective POC diagnostic system that has high sensitivity, portability, multiplexing capability and that can easily extract infectious biomarkers from clinical samples.

Nanoparticle based techniques such as QD barcode and multicomponent nucleic acid enzyme (MNAzyme) based gold nanoparticle (GNP) assays are promising detection platform that can address these demands.

The applicant has developed more than 100 QD barcodes to demonstrate high multiplexing capability, a microfluidic device was fabricated to automate the assay procedure, and a handheld signal read-out system was developed to establish portability. Nevertheless, there are challenges still remaining with current QD barcode technology that need to be addressed prior to clinical validation. The two main challenges are the lack of a PCR-less signal amplification strategy and an effective POC DNA extraction system.

The following examples address the aforementioned challenges. One example illustrates the development of a nanoparticle based isothermal amplification assay to develop an ultrasensitive multiplexed diagnostic platform. Another example illustrates the development of an automated DNA extraction technique by incorporating magnetic microbeads with a microfluidic device. The final example illustrates validate improved sensitivity and automated DNA extraction technique with HPV clinical samples.

Example 3

In this example, recombinase polymerase amplification (RPA) is integrated with QD barcode assay for ultrasensitive detection of three synthetic DNA samples designed specifically for HPV-16, HPV-18, and HPV-58 infections. These HPV types are classified as "high-risk" due to the association with cervical cancer, and about 70% of the total cervical cancer cases are estimated to be linked with HPV-16 and HPV-18 infections [Sz-Hau Chen; Kun-I Lin; Chuan-Yi Tang; Sheng-Lung Peng; Yao-Chen Chuang; Yi-Rou Lin; Jui-Ping Wang; Chih-Sheng Lin Optical Detection of Human Papillomavirus Type 16 and Type 18 by Sequence Sandwich Hybridization With Oligonucleotide-Functionalized Au Nanoparticles. IEEE Trans.on Nanobioscience 8, 120-131; Pons-Salort, M.; Letort, V.; Favre, M.; Heard, I.; Dervaux, B.; Opatowski, L.; Guillemot, D. Exploring individual HPV coinfections is essential to predict HPVvaccination impact on genotype distribution: A model-based approach. Vaccine 2013, 31, 1238-1245]. Also, it has been suggested that subjects with incident HPV-16 or HPV-18 infections have 5-7 times greater chance of developing a subsequent HPV-58 infection compared to subjects not infected with HPV-16 or HPV-18 [Mendez, F.; Nubia, M.; Posso, H.; Molano, M.; Moreno, V.; van den Brule, A. J. C.; Ronderos, M.; Meijer, C.; Munoz, A. Cervical Coinfection with Human Papillomavirus (HPV) Types and Possible Implications for the Prevention of Cervical Cancer by HPV Vaccines. 2005, 1-8], necessitating development of a multiplexed detection platform for various HPV types. The detection limit of QD barcode assay with RPA will be measured for the three targets and compared with conventional QD barcode assay without the amplification. Multiplexed amplification and detection will also be demonstrated by spiking the sample with multiple targets followed by RPA and QD barcode assay. Lastly, asymmetric RPA will be investigated to simplify the overall assay procedure.

Method

A) Synthesis of QD Barcodes

Three QD barcodes (B1, B2 and B3) are synthesized using previously established CCFF method 31. Briefly, a nozzle has two inputs that accept two types of flow: focusing flow of water and focused flow of QDs mixed with copolymer (polystyrene maleic anhydride) in chloroform. Two flows intersect at the output of the nozzle, and polymeric microbeads containing QDs are synthesized due to microfluidic instabilities. Three different ratios of Cadmium Selenide-Zinc Sulfide (CdSe—ZnS) core-shell QDs emitting at 560 nm (QD560) and 640 nm (QD640) will be mixed with 1 mL of 4% polymer solution. Water will be injected to the nozzle at a flow rate of 180 mL/h, and polymer-QD solution will be injected at a rate of 0.9 mL/h to synthesize approximately 3 um beads. After the synthesis, beads will be hardened by overnight stirring and concentrated. The size distribution and concentration of the beads will be measured with Vi-CELL Cell Viability Analyzer.

Each QD barcodes (B1, B2 and B3) is conjugated with corresponding capture DNA strands (C1, C2 and C3) via carbodiimide chemistry. C1, C2 and C3 capture DNA sequences are designed to be complementary to half of HPV-16, HPV-18 and HPV-58 target sequences respectively. For each conjugation, 1 million beads are mixed with 28.8 pmol capture DNA and 9.6 mg of N-(3-Dimethylaminopropyl)-N'-ethylcarbodiimide hydrochloride (EDC) in 2-(Nmorpholino) ethanesulfonic acid buffer (100 mM MES, pH 5) and rotated overnight. The conjugation efficiency is measured using the depletion method. In brief, 10 uL of the supernatant solution from the overnight conjugation is extracted and activated with 190 μL 0.5×SYBR Gold for 10 minutes. The fluorescence signal is measured using a microplate reader and compared with no conjugation control sample (water added in place of beads). The reduction in fluorescence signal compared to no conjugation control sample estimates the amount of unbound capture DNA.

B) Detection Limit of QD Barcode Assay with and without RPA

Serial dilutions are made from synthetic DNA samples designed for HPV-16, HPV-18 and HPV-58 infections ranging from 10 pmol/uL to 1 zmol/uL. Several forward and reverse primer sequences are investigated to find the best primer combinations. For each optimization reaction, 29.5 uL rehydration buffer, 2.4 uL forward primer (10 pmol/uL), 2.4 uL reverse primer (10 pmol/uL), 12.2 uL distilled and deionized (DD) water and 1 uL template DNA (1 amol/uL) are mixed with the enzyme pellet. Reaction is initiated with the addition of 2.5 uL magnesium acetate (MgAc, 280 mM) followed by incubation at 37 deg C. for 30 minutes. Amplicons are purified using a silica membrane-based spin column, and analyzed with agarose gel electrophoresis (3%, 135 V for 1 h). Primer pairs that give the brightest band on gel are used throughout subsequent experiments.

For detection limit measurement of RPA, 1 uL of 0, 1 zmol, 10 zmol, 100 zmol, 1 amol, 10 amol, 100 amol, and 1 fmol copies of HPV-16, HPV-18 or HPV-58 DNA are added to each RPA reaction and incubated at 37deg C. for 30 minutes. Amplicons from each sample are purified and analyzed with gel electrophoresis. Purified amplicons are denatured at 100 deg C. for 10 minutes and used directly in QD barcode assay. For each assay, 1 uL amplicons, 1 uL detection probe (100 pmol/uL), 1 uL microbeads (10000 beads), 7 uL DD water, and 10 uL of hybridization buffer containing 10× saline-sodium citrate (SSC) and 0.1% sodium dodecyl sulfate (SDS) are mixed and incubated at 37 deg C. for 30 minutes. After incubation, samples are washed two times using washing buffer (0.5×SSC+0.1% SDS) and microfilter plates, and resuspended in phosphate buffered saline with Tween (PBST). The fluorescence intensity is measured using a flow cytometer and analyzed with FlowJo software. The median intensity is used to compare change in fluorescence signal between samples. The limit of detection (LOD) is determined as the amount of template DNA at which the median fluorescence intensity is greater than no template control (NTC) signal plus 3 times the standard deviation. Similarly, the detection limit of conventional QD barcode assay is determined. Each assay contains 1 µL of non-amplified template DNA ranging from 0 to 1 fmol copies of HPV-16, HPV-18 or HPV-58 DNA, 1 µL detection probe (100 pmol/uL), 1 µL microbeads (10000 beads), 7 µL DD water, and 10 µL of hybridization buffer. After incubation at 37 deg C. for 30 minutes, each sample is washed twice with washing buffer and resuspended in PBST buffer for flow cytometry.

C) Multiplexed RPA and Multiplexed Detection With QD Barcode Assay

For each multiplexed amplification, 0.8 µL forward primer (10 pmol/µL) and 0.8 µL reverse primer (10 pmol/µL) for HPV-16, HPV-18 and HPV-58 targets are mixed with 3 µL template DNA, 29.5 µL rehydration buffer, 10.2 µL DD water and enzyme pellet. A variety of template DNA combinations are investigated as demonstrated in Table 2. For negative conditions, 1 µL of DD water is added instead, and for positive conditions 1 µL of corresponding template DNA (1 amol/µL) is added to the reaction making up a total of 3 µL template DNA.

TABLE 2

Multiplexing Combinations for Aim I

| Combinations | HPV-16 | HPV-18 | HPV-58 |
|---|---|---|---|
| 1 | − | − | − |
| 2 | + | − | − |
| 3 | − | + | − |
| 4 | − | − | + |
| 5 | + | + | − |
| 6 | + | − | + |
| 7 | + | + | + |

The reaction are initiated with the addition of 2.5 µL magnesium acetate (MgAc, 280 mM) followed by incubation at 37 deg C. for 30 minutes. Amplicons are purified using a silica membrane-based spin column, and analyzed with agarose gel electrophoresis (3%, 135 V for 1 h). Purified amplicons are denatured at 100 deg C. for 10 minutes and used directly in QD barcode assay. For each multiplexed assay, 3 µL amplicons, 3 µL detection probe (80 pmol/uL), 1 uL B1 (10000 beads), 1 uL B2 (10000 beads), 1 uL B3 (10000 beads), 1 uL DD water, and 10 uL of hybridization buffer (10×SSC+0.1% SDS) are mixed and incubated at 37 deg C. for 30 minutes. After incubation, samples are washed two times using washing buffer (0.5× SSC+0.1% SDS) and microfilter plates, and resuspended in PBST buffer. The fluorescence signal is measured using a flow cytometer. The acquired data is plotted with FlowJo software based on fluorescence intensity (FL2 versus FL1 signal), and gated to separate each barcode signal. The median intensity is calculated from the gated populations and this value is used to determine whether there is a positive or negative signal based on the same detection limit criterion used previously.

D) Asymmetric RPA

Asymmetric RPA is investigated by using limiting amount of reverse primers and excess amount of forward primers in RPA reaction. In brief, each RPA reaction contains 2.4 µL forward primer (10 pmol/µL), 29.5 µL rehydration buffer, 1 µL template DNA (1 amol/µL), 12.2 µL DD water and enzyme pellet. Various concentrations of reverse primer are added to the reaction ranging from 2.4 µL of 10 pmol/µL to 1 fmol/µL. The amplicons are directly used in QD barcode assay without further denaturation by following the same protocol explained above. The fluorescence signal is measured using a flow cytometer, and the median intensity compared to find the optimal primer concentrations. Each product is purified and visualized on gel electrophoresis using the same protocol explained previously.

2.1.3 Results

Detection of zeptomole copies of DNA at an isothermal condition may be achieved (see FIGS. 11-15). Synthesized QD barcodes are expected to have monodispersed size around 3 µm. RPA may significantly improve the analytical sensitivity of QD barcode assay, and achieve 1 zmol limit of detection. Furthermore, multiplexed isothermal amplification of three genetic targets (HPV-16, HPV-18 and HPV-58) may be demonstrated with RPA, and the amplified products from RPA may be used in QD barcode assay for multiplexed detection. Lastly, asymmetric RPA may produce single-stranded amplicons, which may directly be used in the assay without further denaturation.

Example 4

Development of an Automated DNA Extraction Device

A microfluidic device was fabricated to automate DNA extraction from cervical cells as illustrated in FIG. 3. Crude sample is first injected to the microfluidic channel, and stopped by the first gate. Lysis buffer is added to disrupt the cell membrane, which releases cellular components to pass through the first gate. Magnetic beads are added along the channel, which will electrostatically bind DNA from cell lysate and collected at the second gate. Washing buffer is added to remove contaminants, and elution buffer will be added to release DNA from magnetic beads. The chip dimensions and location of the magnets were examined to achieve optimized reaction between magnetic beads and cell lysate. Lastly, the extraction efficiency of the automated device is assessed by quantitative PCR and compared with manual extraction kits.

A) Fabrication of Micrometer-Size Device

The dimensions of the channel, which may be a microfluidic channel, are estimated using Poiseuille equation to allow laminar flow and sufficient reaction time between magnetic beads and cell lysate (~5 minutes). The dimensions of the channel may range in size from micro to centimeters. The reaction channel between the first and second gates may be about 60 mm long, about 600 µm wide and about 15 µm deep. Assuming that vertical fluid pressure is the only pressure driving the flow, and that the viscosity (p) and density (p) will be similar to water (0.01 g/cm!s and 1000 kg/m³ respectively), hydrodynamic resistance (RH), volumetric flow rate (Q), fluid velocity (V) and reaction time (T) are estimated as the following:

$$R_H = \frac{12*\mu*L}{h^3*w} = 3.56 \times 10^{14} \text{ kg/m}^4 \cdot \text{s} \quad \text{Equation (1)}$$

$$Q = \frac{-\rho*g*h}{R_H} = 1.65 \times 10^{-12} \text{ m}^3/\text{s} \quad \text{Equation (2)}$$

$$V = \frac{Q}{\text{Cross sectional area}} = 1.84 \times 10^{-4} \text{ m/s} \quad \text{Equation (3)}$$

$$T = \frac{\text{Reaction channel length}}{V} = 326 \text{ s} = 5.4 \text{ minutes} \quad \text{Equation (4)}$$

The micrometer-size chip, which may be a microfluidic chip, may be fabricated in polydimethylsiloxane (PDMS) using soft lithography [14, 15]. The microfluidic chip may also be made of glass. The channels will be first drawn in computer-aided design (CAD) program to print a transparency, which serves as a photomask in contact photolithography to create a positive relief of master photoresist on silicon wafer. Prepolymer is casted against this master to generate a negative PDMS replica of the master. During this stage, posts are placed at the channel inlets and outlets of the master to create access holes. After replica molding, PDMS is peeled from the master and sealed irreversibly with a micro cover glass by plasma-oxidation, and steel tubes are glued into access holes to connect syringes with the chip. Two permanent magnets (Magnet #1 330 and magnet #2 332) will be put into PDMS replica beside the reaction channel as demonstrated in FIG. 3. The location of these magnets may be determined to result in optimized flow rate of magnetic beads and mixing with cell lysate. The third magnet 334 is placed directly under the channel at the second gate as shown in FIG. 3. The gates are patterned into PDMS channel during soft lithography. The first gate is composed of cubic blocks (5 µm³) separated apart by about 5 µm, and the second gate is composed of cubic blocks (0.2 µm³) separated apart by about 0.2 µm.

B) Sample Collection

Clinical samples are collected from cervix of healthy subjects and supplied by a clinical collaborator (Dr. Anu Rebbapragada at Gamma-DynaCare Medical Laboratories). Briefly, a spatula is used to scrape the cervical tissue and a brush is used to collect cells scraped off from cervix. The sample is stored in sterile saline at −20 deg C. until use.

C) Extraction Efficiency

Extraction efficiency of the device is assessed by running the automated extraction with various concentrations of clinical samples (102 to 106 cells/mL). Briefly, with reference to FIG. 3, the microfluidic device 300 is positioned vertically (sample inlet facing up) on a clamp stand and each inlet are connected to a syringe through a plastic tube. Sample 301 and reagents will be pulled down to the channel by gravitational force. Magnetic beads 320 and cell lysate 307 react within reaction channel 302 for approximately five minutes and settle at the second gate. Once all beads settle at the second gate 304 or the third magnet 334, contaminants are washed away, and the device will be rotated 90 degrees counter-clock wise to position the elution buffer inlet 315 facing up. The elution buffer 314 will be injected to the channel in the same manner, and extracted DNA 308 will be collected at the outlet 316. DNA yield is quantified by measuring the absorbance of extracted product at 260 nm and purity is examined by measuring 260/280 absorbance ratio. Lastly, betaglobin sequences in extracted genomic DNA is amplified by real-time quantitative PCR by mixing 1 uL forward primer (10 uM), 1 uL reverse primer (10 uM), 10 uL extracted DNA, 1 uL dNTPs (10 mM), 0.25 uL Taq DNA polymerase, 5 µL PCR buffer and 31.75 uL nuclease-free water followed by initial denaturation at 95 deg C. for 30 seconds, 30 cycles of incubation at 95 deg C. for 30 seconds and 68 deg C. for 60 seconds, and final extension at 68 deg C. for 5 minutes. PCR products are validated by running agarose gel electrophoresis (3%, 135 V for 1 h). The time required to reach the exponential phase is plotted against the cell concentration to compare the extraction efficiency between automated microfluidic device and commercially available manual kits.

An automated DNA extraction system, which has a microfluidic channel to disrupt cell membrane, allow electrostatic binding of genomic DNA to magnetic beads, remove other cellular components, and collect isolated DNA from the beads has been obtained. The proposed dimensions acquire sufficient reaction time (~5 minutes) between the beads and lysate, and the magnetic fields imposed by permanent magnets direct the flow of beads to adequately interact with the cellular components and washing buffer. Also, it is expected that the time required to reach the exponential phase in qPCR may be faster with increasing cell concentration. Finally, the automated DNA extraction device is expected to achieve similar extraction efficiency as compared to manual extraction of commercially available magnetic bead technology.

Example 5

Figure 16:
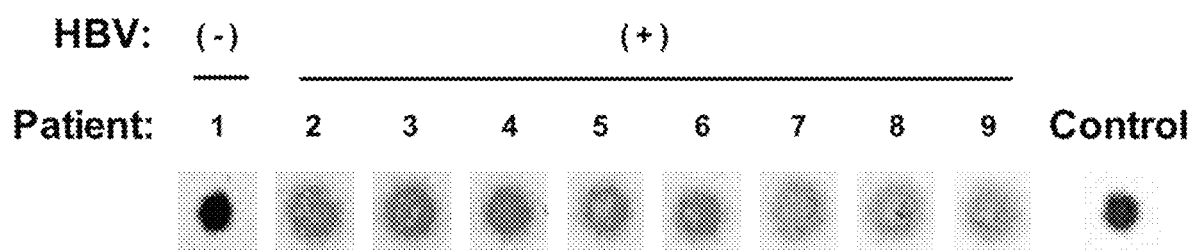
FIG. 16 illustrates detection of genetic HBV markers in clinical patient samples using MNAzyme-GNP assay that includes RPA signal amplification module.

Detection of Genetic HBV Markers in Clinical Patient Samples Using MNAzyme-GNP Assay This invention describes a diagnostic platform for detection of viral, bacterial, protozoan, fungal and other infections, which allows an exponential amplification of target nucleic acid at an isothermal condition and colorimetric detection of infectious genetic biomarkers using Recombinase Polymerase Amplification (RPA) and Multicomponent Nucleic Acid enzyme (MNAzyme) based gold nanoparticle (GNP) colorimetric assay (MNAzyme-GNP assay) respectively. RPA is an isothermal nucleic acid amplification technique, which uses recombinase enzymes to nucleate onto single-stranded oligonucleotides and form nucleoprotein filaments, which then self-assemble onto double-stranded DNA scaffold to initiate nucleic acid amplification. The self-assembly process of nucleoprotein filaments allows target nucleic acid to get amplified at an isothermal condition, and thus avoids the use of an expensive thermocycler for precise temperature control. Mz-GNP assay is formed by GNPs whose surface is modified with DNA capture strands. A linker oligonucleotide is designed to have its two ends hybridize to capture strands and crosslink GNPs, which results in purple color of the solution. When nucleic acid amplified by RPA is present, it activates MNAzyme. Active MNAzyme cleaves the Linker strands holding GNPs together. GNPs get dispersed and solution turns red, providing a simple colorimetric readout of genetic target presence. Different MNAzymes specific for particular targets can function in parallel allowing a number of pathogens to be detected in the same assay. Integration of RPA with MNAzyme-based gold nanoparticle assay will provide high sensitivity while maintaining rapid and cost-effective colorimetric diagnostics for laboratory and point-of-care applications. FIG. 16 illustrates the detection of genetic HBV markers in clinical patient samples using MNAzyme-GNP assay that includes RPA signal amplification module. One negative (1) and 8 positive (2-9) samples were sampled. Presence of the marker was confirmed by a standard qPCR assay. Negative water control was included. Results are presented as 3 μL drops on thin layer chromatography (TLC) plates.

REFERENCES

1. Giri, S., Sykes, E. A., Jennings, T. L. & Chan, W. C. W. Rapid screening of genetic biomarkers of infectious agents using quantum dot barcodes. ACS Nano 5, 1580-7 (2011).
2. Klostranec, J. M. et al. Convergence of quantum dot barcodes with microfluidics and signal processing for multiplexed high-throughput infectious disease diagnostics. Nano Lett. 7, 2812-8 (2007).
3. Han, M., Gao, X., Su, J. Z. & Nie, S. Quantum-dot-tagged microbeads for multiplexed optical coding of biomolecules. Nat. Biotechnol. 19, 631-5 (2001).
4. Fournier-Bidoz, S. et al. Facile and rapid one-step mass preparation of quantum-dot barcodes. Angew. Chem. Int. Ed. Engl. 47, 5577-81 (2008).
5. Walt, D. R. Fibre optic microarrays. Chem. Soc. Rev. 39, 38-50 (2010).
6. Piepenburg, O., Williams, C. H., Stemple, D. L. & Armes, N. a. DNA detection using recombination proteins. PLoS Biol. 4, e204 (2006).
7. Liong, M. et al. Magnetic barcode assay for genetic detection of pathogens. Nat. Commun. 4, 1752 (2013).
8. Zhu, H., Mavandadi, S., Coskun, A. F., Yaglidere, O. & Ozcan, A. Optofluidic fluorescent imaging cytometry on a cell phone. Anal. Chem. 83, 6641-7 (2011).
9. Peng, X., Schlamp, M. C., Kadavanich, A. V & Alivisatos, A. P. Epitaxial Growth of Highly Luminescent CdSe/CdS Core/Shell Nanocrystals with Photostability and Electronic Accessibility. J. Am. Chem. Soc. 119, 7019-7029 (1997).
10. Hines, M. A. & Guyot-Sionnest, P. Synthesis and Characterization of Strongly Luminescing ZnSCapped CdSe Nanocrystals. J. Phys. Chem. 100, 468-471 (1996).
11. Smith G J D et al. (2009) Dating the emergence of pandemic influenza viruses. Proceedings of the National Academy of Sciences of the United States of America 106:11709-12.
12. Yerly S et al. (2001) Nosocomial outbreak of multiple bloodborne viral infections. The Journal of Infectious Diseases 184:369-72.
13. Chu C et al. (2001) Hepatitis C: Comparison with acute hepatitis B—Comparison of clinical, 355 virologic and pathologic features in patients with acute hepatitis B and C. Journal of Gastroenterology and Hepatology 16:209-214.
14. McDonald, J. C.; Duffy, D. C.; Anderson, J. R.; Chiu, D. T.; Wu, H.; Schueller, O. J. A.; Whitesides, G. M. Fabrication of microfluidic systems in poly(dimethylsiloxane). Electrophoresis 2000, 21, 27-40.
15. Duffy, D. C.; McDonald, J. C.; Schueller, O. J. A.; Whitesides, G. M. Rapid Prototyping of Microfluidic Systems in Poly(dimethylsiloxane). Anal. Chem. 1998, 70, 4974-4984.

Although the description above contains many specificities, these should not be construed as limiting the scope of the invention but as merely providing illustrations of some of the presently preferred embodiments of this invention. Thus, the scope of the invention should be determined by the appended claims and their legal equivalents, rather than by the examples given.

Without further elaboration, it is believed that one of ordinary skill in the art can, based on the description presented herein, utilize the present invention to the full extent. All publications cited herein are incorporated by reference in their entirety.

Therefore what is claimed is:

1. An automated portable multiplex detector device for use at point-of-care (POC) setting to simultaneously detect the presence of multiple targets of interest in a sample, the portable device including:
   (a) a PCR-less nucleic acid amplification compartment for amplifying nucleic acid of each of the multiple targets of interest in the sample,
   (b) an analysis compartment in communication with the amplification compartment, the analysis compartment housing a nanoparticle-based multiplex detector configured for receiving the amplified nucleic acid of each of the multiple targets of interest from the amplification compartment and producing at least one optical signal that correlates the amplified nucleic acid with the presence of the multiple targets of interest in the sample, the nanoparticle-based multiplex detector comprising:
      (i) quantum dot barcodes deposited on the surface of a microwell chip,
      (ii) a secondary probe,
      (iii) a capture ligand, and
      (iv) a detection ligand,
   configured for performing a QD barcode assay to produce the at least one optical signal,
   (c) a wireless communication device for imaging and analyzing the at least one optical signal, the wireless communication device having a camera, a display, and a movable objective means disposed between the microwell chip and the camera of the wireless communication device for collecting the at least one optical signal and to focus the at least one optical signal to the camera of the wireless communication device to be viewable on the display of the wireless communication device,
   (d) a nucleic acid extraction compartment in communication with the amplification compartment for delivering extracted nucleic acid to the amplification compartment, the extraction compartment comprising a main extraction channel having a receiving end and a dispensing end, the main extraction channel comprising, in sequence from the receiving end:
      (i) a lysis zone fluidly connected to a sample delivery inlet and a lysis buffer inlet;
      (ii) a binding zone fluidly connected to a magnetic bead and binding buffer inlet, the binding zone being separated from the lysis zone by a first gate;
      (iii) a washing zone fluidly connected to a washing buffer inlet;
      (iv) an elution zone fluidly connected to an elution buffer inlet and a first outlet for releasing extracted nucleic acid, wherein said elution buffer inlet and said first outlet are each perpendicularly connected to said main extraction channel directly opposite and in fluid communication to one another, such that rotation of the device about 90 degrees orients the elution buffer inlet and first outlet in a vertical position; and
      (v) a second outlet for releasing waste at the dispensing end, the second outlet being separated from the main extraction channel by a second gate; and
   (e) a reagent storage compartment in communication with the nucleic acid extraction compartment and with the nucleic acid amplification compartment for delivering reagents to the nucleic acid extraction compartment and to the nucleic acid amplification compartment, the reagent storage compartment including sub-compartments containing amplification reagents necessary for an isothermal recombinase polymerase amplification assay and sub-compartments containing buffers and reagents necessary for nucleic acid extraction.

2. The device of claim 1, wherein the nucleic acid amplification compartment includes one or more amplification reaction channels and amplification reagent delivery inlets extending from the amplification reaction channels, the amplification reagent delivery inlets being in communication with the reagent storage compartment for delivering the nucleic acid amplification reagents to the amplification reaction channel.

3. The device of claim 1, wherein the sub-compartments containing buffers and reagents necessary for nucleic acid extraction, comprise:
   a sub-compartment having a lysis buffer fluidly connected to the main extraction channel by the lysis buffer inlet,
   a sub-compartment having magnetic beads and binding buffer fluidly connected to the main extraction channel by the magnetic bead and binding buffer inlet, and
   a sub-compartment having washing buffer fluidly connected to the main extraction channel by the washing buffer inlet,
   wherein each of the buffers and reagents necessary for nucleic acid extraction is sequentially delivered to the main extraction channel.

4. The device of claim 1, wherein the sample delivery inlet is configured for receiving a sample containing the nucleic acid to be extracted.

5. The device of claim 1, further comprising one or more permanent magnets distributed along the main extraction channel for directing the magnetic beads to the elution zone.

6. The device of claim 1, wherein the optical signal is a quantifiable color or fluorescence signal of the amplified nucleic acid.

7. The device of claim 1, wherein the reagents are stored in the reagent storage compartment in solution, lyophilized or powder form.

8. The device of claim 1, wherein the communication is fluid communication.

9. A method of simultaneously detecting the presence or absence of multiple targets of interest in a sample, the method including: (a) providing a device of claim 1, (b) amplifying the nucleic acid of the multiple targets of interest in the sample in the amplification compartment, (c) contacting the amplified nucleic acid with the nanoparticle-based multiplex detector to generate the optical signal, and (d) correlating the optical signal of the amplified nucleic acid with the presence or absence of the multiple targets of interest in the sample.

10. The method of claim 9, wherein prior to the amplification step (b), the method includes an extraction step comprising (i) positioning the device such that the extraction channel is vertically positioned for delivery of the sample and reagents, (ii) rotating the device by about 90 degrees to orient the elution buffer inlet and first outlet of the extraction channel to a vertical position to elute the extracted nucleic acid of the multiple targets of interest from the sample and deliver the extracted nucleic acid to the amplification compartment.

11. The method of claim 9, wherein the amplification of the nucleic acid of step (b) is an isothermal recombinase polymerase amplification assay.

12. The method of claim 9, wherein the multiplex detector includes different populations of primary probes having nanoparticles and secondary probes, each population corresponding to one specific target, the primary and secondary probe of each population having a ligand that binds to nucleic acid characteristic of the population's target, such as in the presence of the nucleic acid of the population's target a complex is formed between the primary probe, the secondary probe and the nucleic acid of said target, the complex generating two signals, a first signal emitted from the first probe which distinguishes the identity of the population's target, and a second signal emitted from the second probe which identifies the presence or absence of the population's target, and the method further comprises (c) exciting the different populations of primary and secondary probes to generate corresponding first and second signals; and (d) reading the first and second signals from the populations of primary and secondary labels, whereby the presence of a first and second signal in one population is indicative of the identity and presence of said population's target in the sample.

13. The method of claim 9, wherein the multiplex detector comprises (i) a nucleic acid substrate, (ii) a pre-catalytic nucleic acid subunit, the pre-catalytic nucleic acid subunit including a sensor domain configured for binding to at least a portion of the biological target, and a catalytic domain which catalyzes the nucleic acid substrate solely when the target is bound to the sensor domain, and (iii) gold nanoparticles (GNPs), the GNPs functionalized with a linking moiety for crosslinking with the nucleic acid substrate in the absence of the target; and (b) optically analyzing the sample to determine whether the GNPs substantially crosslinked with the nucleic acid substrate, wherein when crosslinked with the nucleic acid substrate the GNPs turn the sample to a first color, and in the presence of the target, GNPs turn the sample to a second color indicative that the target is present in the sample.

* * * * *

SEQUENCE LISTING

<160> NUMBER OF SEQ ID NOS: 36

<210> SEQ ID NO 1
<211> LENGTH: 32
<212> TYPE: DNA
<213> ORGANISM: Artificial Sequence
<220> FEATURE:
<223> OTHER INFORMATION: Synthetic

<400> SEQUENCE: 1
ggcatggaca ttgaccctta taaagaatttt gg        32

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
tgtcgagaag gtcccgaata gacggaaaga        30

<210> SEQ ID NO 3
<211> LENGTH: 32
<212> TYPE: DNA
<213> ORGANISM: Artificial Sequence
<220> FEATURE:

<223> OTHER INFORMATION: Synthetic

<400> SEQUENCE: 3
gaaaggtgaa ggggcagtag taatacaaga ca                             32

<210> SEQ ID NO 4
<211> LENGTH: 32
<212> TYPE: DNA
<213> ORGANISM: Artificial Sequence
<220> FEATURE:
<223> OTHER INFORMATION: Synthetic

<400> SEQUENCE: 4
ccacacaatc atcacctgcc atctgttttc ca                             32

<210> SEQ ID NO 5
<211> LENGTH: 30
<212> TYPE: DNA
<213> ORGANISM: Artificial Sequence
<220> FEATURE:
<223> OTHER INFORMATION: Synthetic

<400> SEQUENCE: 5
ccctcttagt ttgcatagtt tcccgttatg                                30

<210> SEQ ID NO 6
<211> LENGTH: 58
<212> TYPE: DNA
<213> ORGANISM: Artificial Sequence
<220> FEATURE:
<223> OTHER INFORMATION: Synthetic

<400> SEQUENCE: 6
cggcgatgaa tacctagcac acttactaca taacgggaaa ctatgcaaac taagaggg   58

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
taagtgtgct aggtattcat cgccg                                     25

<210> SEQ ID NO 8
<211> LENGTH: 30
<212> TYPE: DNA
<213> ORGANISM: Artificial Sequence
<220> FEATURE:
<223> OTHER INFORMATION: Synthetic

<400> SEQUENCE: 8
acttggttgt ttggggggga gttgaattca                                30

<210> SEQ ID NO 9
<211> LENGTH: 58
<212> TYPE: DNA
<213> ORGANISM: Artificial Sequence
<220> FEATURE:
<223> OTHER INFORMATION: Synthetic

<400> SEQUENCE: 9
cggcgatgaa tacctagcac acttactatg aattcaactc cccccaaac aaccaagt   58

<210> SEQ ID NO 10
<211> LENGTH: 30
<212> TYPE: DNA
<213> ORGANISM: Artificial Sequence
<220> FEATURE:
<223> OTHER INFORMATION: Synthetic

<400> SEQUENCE: 10
ccattccctg ccatcctccc tctataaaac                              30

<210> SEQ ID NO 11
<211> LENGTH: 58
<212> TYPE: DNA
<213> ORGANISM: Artificial Sequence
<220> FEATURE:
<223> OTHER INFORMATION: Synthetic

<400> SEQUENCE: 11
cggcgatgaa tacctagcac acttactagt tttatagagg gaggatggca gggaatgg      58

<210> SEQ ID NO 12
<211> LENGTH: 27
<212> TYPE: DNA
<213> ORGANISM: Artificial Sequence
<220> FEATURE:
<223> OTHER INFORMATION: Synthetic

<400> SEQUENCE: 12
caccgcagtt tcagctgctc gaattgg                                 27

<210> SEQ ID NO 13
<211> LENGTH: 55
<212> TYPE: DNA
<213> ORGANISM: Artificial Sequence
<220> FEATURE:
<223> OTHER INFORMATION: Synthetic

<400> SEQUENCE: 13
cggcgatgaa tacctagcac acttactacc aattcgagca gctgaaactg cggtg          55

<210> SEQ ID NO 14
<211> LENGTH: 25
<212> TYPE: DNA
<213> ORGANISM: Artificial Sequence
<220> FEATURE:
<223> OTHER INFORMATION: Synthetic

<400> SEQUENCE: 14
taagtgtgct aggtattcat cgccg                                   25

<210> SEQ ID NO 15
<211> LENGTH: 33
<212> TYPE: DNA
<213> ORGANISM: Artificial Sequence
<220> FEATURE:
<223> OTHER INFORMATION: Synthetic

<400> SEQUENCE: 15
gagaccatca atgaggaagc tgcagaatgg gat                          33

<210> SEQ ID NO 16
<211> LENGTH: 61
<212> TYPE: DNA
<213> ORGANISM: Artificial Sequence
<220> FEATURE:
<223> OTHER INFORMATION: Synthetic

<400> SEQUENCE: 16
cggcgatgaa tacctagcac acttactaat cccattctgc agcttcctca ttgatggtct    60
c    61

<210> SEQ ID NO 17
<211> LENGTH: 25
<212> TYPE: DNA
<213> ORGANISM: Artificial Sequence
<220> FEATURE:
<223> OTHER INFORMATION: Synthetic

<400> SEQUENCE: 17
tcagaaggca aaaagagag taact    25

<210> SEQ ID NO 18
<211> LENGTH: 53
<212> TYPE: DNA
<213> ORGANISM: Artificial Sequence
<220> FEATURE:
<223> OTHER INFORMATION: Synthetic

<400> SEQUENCE: 18
cggcgatgaa tacctagcac acttactaag ttactctctt ttttgccttc tga    53

<210> SEQ ID NO 19
<211> LENGTH: 26
<212> TYPE: DNA
<213> ORGANISM: Artificial Sequence
<220> FEATURE:
<223> OTHER INFORMATION: Synthetic

<400> SEQUENCE: 19
catagtggtc tgcggaaccg gtgagt    26

<210> SEQ ID NO 20
<211> LENGTH: 54
<212> TYPE: DNA
<213> ORGANISM: Artificial Sequence
<220> FEATURE:
<223> OTHER INFORMATION: Synthetic

<400> SEQUENCE: 20
cggcgatgaa tacctagcac acttactaac tcaccggttc cgcagaccac tatg    54

<210> SEQ ID NO 21
<211> LENGTH: 25
<212> TYPE: DNA
<213> ORGANISM: Artificial Sequence
<220> FEATURE:
<223> OTHER INFORMATION: Synthetic

<400> SEQUENCE: 21
taagtgtgct aggtattcat cgccg    25

<210> SEQ ID NO 22
<211> LENGTH: 22
<212> TYPE: DNA
<213> ORGANISM: Artificial Sequence
<220> FEATURE:
<223> OTHER INFORMATION: Synthetic

<400> SEQUENCE: 22
gacaatgctc actgaggata gt    22

```
<210> SEQ ID NO 23
<211> LENGTH: 50
<212> TYPE: DNA
<213> ORGANISM: Artificial Sequence
<220> FEATURE:
<223> OTHER INFORMATION: Synthetic

<400> SEQUENCE: 23
cggcgatgaa tacctagcac acttactaac tatcctcagt gagcattgtc         50

<210> SEQ ID NO 24
<211> LENGTH: 15
<212> TYPE: DNA
<213> ORGANISM: Artificial Sequence
<220> FEATURE:
<223> OTHER INFORMATION: Synthetic

<400> SEQUENCE: 24
ccaatatcgg cggcc                                                15

<210> SEQ ID NO 25
<211> LENGTH: 43
<212> TYPE: DNA
<213> ORGANISM: Artificial Sequence
<220> FEATURE:
<223> OTHER INFORMATION: Synthetic

<400> SEQUENCE: 25
cggcgatgaa tacctagcac acttactagg ccgccgatat tgg                 43

<210> SEQ ID NO 26
<211> LENGTH: 116
<212> TYPE: DNA
<213> ORGANISM: Artificial Sequence
<220> FEATURE:
<223> OTHER INFORMATION: Synthetic

<400> SEQUENCE: 26
gaaaggtgaa ggggcagtag taatacaaga caatagtgac ataaaggtag taccaagaag  60
aaaagcaaag atcattaggg attatggaaa acagatggca ggtgatgatt gtgtgg    116

<210> SEQ ID NO 27
<211> LENGTH: 66
<212> TYPE: DNA
<213> ORGANISM: Artificial Sequence
<220> FEATURE:
<223> OTHER INFORMATION: Synthetic

<400> SEQUENCE: 27 ttttttttg ccacacaatc atcacctgcc atctgttttc cataatccct aatgatcttt   60
gctttt                                                            66

<210> SEQ ID NO 28
<211> LENGTH: 57
<212> TYPE: DNA
<213> ORGANISM: Artificial Sequence
<220> FEATURE:
<223> OTHER INFORMATION: Synthetic

<400> SEQUENCE: 28
ttggtactac ctttatgtca ctattgtctt gtattactac tgccccttca cctttcc    57

<210> SEQ ID NO 29
<211> LENGTH: 100
<212> TYPE: DNA
```

<213> ORGANISM: Artificial Sequence
<220> FEATURE:
<223> OTHER INFORMATION: Synthetic

<400> SEQUENCE: 29

```
ggcatggaca ttgaccctta taaagaattt ggagcttctg tggagttact ctcttttttg    60
ccttctgatt tctttccgtc tattcgggac cttctcgaca                         100
```

<210> SEQ ID NO 30
<211> LENGTH: 56
<212> TYPE: DNA
<213> ORGANISM: Artificial Sequence
<220> FEATURE:
<223> OTHER INFORMATION: Synthetic

<400> SEQUENCE: 30

```
aaaaaaaaat gtcgagaagg tcccgaatag acggaaagaa atcagaaggc aaaaaa       56
```

<210> SEQ ID NO 31
<211> LENGTH: 47
<212> TYPE: DNA
<213> ORGANISM: Artificial Sequence
<220> FEATURE:
<223> OTHER INFORMATION: Synthetic

<400> SEQUENCE: 31

```
aactccacag aagctccaaa ttctttataa gggtcaatgt ccatgcc                 47
```

<210> SEQ ID NO 32
<211> LENGTH: 22
<212> TYPE: DNA
<213> ORGANISM: Artificial Sequence
<220> FEATURE:
<223> OTHER INFORMATION: Synthetic

<400> SEQUENCE: 32

```
gacaatgctc actgaggata gt                                            22
```

<210> SEQ ID NO 33
<211> LENGTH: 50
<212> TYPE: DNA
<213> ORGANISM: Artificial Sequence
<220> FEATURE:
<223> OTHER INFORMATION: Synthetic

<400> SEQUENCE: 33

```
cggcgatgaa tacctagcac acttactaac tatcctcagt gagcattgtc              50
```

<210> SEQ ID NO 34
<211> LENGTH: 25
<212> TYPE: DNA
<213> ORGANISM: Artificial Sequence
<220> FEATURE:
<223> OTHER INFORMATION: Synthetic

<400> SEQUENCE: 34

```
taagtgtgct aggtattcat cgccg                                         25
```

<210> SEQ ID NO 35
<211> LENGTH: 15
<212> TYPE: DNA
<213> ORGANISM: Artificial Sequence
<220> FEATURE:
<223> OTHER INFORMATION: Synthetic

<400> SEQUENCE: 35

```
ccaatatcgg cggcc                                                             15

<210> SEQ ID NO 36
<211> LENGTH: 43
<212> TYPE: DNA
<213> ORGANISM: Artificial Sequence
<220> FEATURE:
<223> OTHER INFORMATION: Synthetic

<400> SEQUENCE: 36
cggcgatgaa tacctagcac acttactagg ccgccgatat tgg                              43
```